United States Patent [19]

Sieben et al.

[11] Patent Number: 5,438,997
[45] Date of Patent: Aug. 8, 1995

[54] INTRAVASCULAR IMAGING APPARATUS AND METHODS FOR USE AND MANUFACTURE

[76] Inventors: Wayne Sieben, 3707 Nokumis, Apt. 6; Mark J. Whalen, 2001 Ridgewood Dr., both of, Alexandria, Minn. 56308

[21] Appl. No.: 895,094

[22] Filed: Jun. 8, 1992

Related U.S. Application Data

[62] Division of Ser. No. 668,919, Mar. 13, 1991, abandoned.

[51] Int. Cl.⁶ .............................................. A61B 8/12
[52] U.S. Cl. .............................................. 128/662.06
[58] Field of Search .................. 128/4, 662.03, 662.06

[56] References Cited

U.S. PATENT DOCUMENTS

| | | | |
|---|---|---|---|
| 3,542,014 | 11/1970 | Peronneau | 128/2 |
| 3,779,234 | 12/1973 | Eggleton et al. | 128/2 V |
| 3,789,841 | 2/1974 | Antoshkiw | 128/2.05 R |
| 3,827,115 | 8/1974 | Bom | 29/25.35 |
| 3,938,502 | 2/1976 | Bom | 128/2 V |
| 4,494,549 | 1/1985 | Namba et al. | 128/660 |
| 4,517,985 | 5/1985 | Teslawaki et al. | 128/660 |
| 4,545,390 | 10/1985 | Leary | 128/772 |
| 4,582,061 | 4/1986 | Fry | 128/662.05 |
| 4,587,971 | 5/1986 | Stolfi et al. | 128/660 |
| 4,587,972 | 5/1986 | Morantte, Jr. | 128/660 |
| 4,615,330 | 10/1986 | Nagasaki et al. | 128/662.06 |
| 4,664,121 | 4/1987 | Sanghvi et al. | 128/660 |
| 4,671,292 | 6/1987 | Matzuk | 128/660 |
| 4,692,864 | 9/1987 | Shimoni et al. | 364/414 |
| 4,729,384 | 3/1988 | Bazenet | 128/691 |
| 4,732,156 | 3/1988 | Nakamura | 128/660 |
| 4,794,931 | 1/1989 | Yock | 128/660.03 |
| 4,815,470 | 3/1989 | Curtis et al. | 128/662.03 |
| 4,821,731 | 4/1989 | Martinelli et al. | 128/662.06 |
| 4,834,102 | 5/1989 | Schwarschild et al. | 128/662.06 |
| 4,841,977 | 6/1989 | Griffith et al. | 128/660.03 |
| 4,880,009 | 11/1989 | Yanagawa | 128/660.09 |
| 4,887,605 | 12/1989 | Angelsen et al. | 128/660.03 |
| 4,887,606 | 12/1989 | Yock et al. | 128/662.05 |
| 4,899,757 | 2/1990 | Pope, Jr. et al. | 128/662.06 |
| 4,911,170 | 3/1990 | Thomas, III et al. | 128/662.06 |
| 4,911,172 | 3/1990 | Bui et al. | 128/662.06 |
| 4,911,173 | 3/1990 | Terwilliger | 128/662.06 |
| 4,917,097 | 4/1990 | Proudian et al. | 128/662.06 |
| 4,928,699 | 5/1990 | Sasai | 128/4 |
| 4,944,740 | 7/1990 | Buckbinder et al. | 606/194 |
| 4,947,852 | 8/1990 | Nassi et al. | 128/622.06 |
| 4,951,677 | 8/1990 | Crowley et al. | 128/662.06 |
| 4,957,112 | 9/1990 | Yokoi et al. | 128/662.06 |
| 4,977,898 | 12/1990 | Schwarzschild et al. | 128/662.06 |
| 5,000,185 | 3/1991 | Yock | 128/622.03 |

(List continued on next page.)

FOREIGN PATENT DOCUMENTS 5-20158 1/1984 Japan.

OTHER PUBLICATIONS

U.S. Application Ser. No. 07/552,430 dated Jul. 13, 1990, Makinowski.

(List continued on next page.)

*Primary Examiner*—George Manuel
*Attorney, Agent, or Firm*—Merchant, Gould, Smith, Edell, Welter & Schmidt

[57] ABSTRACT

A device for ultrasonic imaging, and methods for the use an manufacture thereof, particularly of small coronary vessels. The device comprises an elongate member with a distal end that can be positioned within a small vessel of a patient's body while a proximal end is located outside the body, a transducer located at a distal end of the elongate member and operable to scan the distal coronary vessels with ultrasonic pulses, and a signal processor connected to a proximal end of the elongate member and to the transducer for generating and receiving pulses to and from the transducer. A motor may be also connected to the proximal end of the elongate member for rotating the transducer.

19 Claims, 12 Drawing Sheets

U.S. PATENT DOCUMENTS

| | | | |
|---|---|---|---|
| 5,002,059 | 3/1991 | Crowley et al. | 128/662.06 |
| 5,010,886 | 4/1991 | Passafaro et al. | 128/660.03 |
| 5,020,539 | 6/1991 | Yokoi et al. | 128/662.06 |
| 5,022,399 | 6/1991 | Biegeleisen | 128/662.06 |
| 5,029,588 | 7/1991 | Yock et al. | 128/622.06 |
| 5,049,130 | 9/1991 | Powell | 128/662.06 |
| 5,052,404 | 10/1991 | Hodgson | 128/772 |
| 5,054,492 | 10/1991 | Scribner et al. | 128/662.06 |
| 5,059,851 | 10/1991 | Corl et al. | 310/344 |
| 5,095,911 | 3/1992 | Pomeranz | 128/662.06 |
| 5,099,850 | 3/1992 | Matsui et al. | 128/662.06 |
| 5,105,818 | 4/1992 | Christian et al. | 128/662.06 |
| 5,108,411 | 4/1992 | McKenzie | 606/159 |
| 5,115,810 | 5/1992 | Watanabe et al. | 128/662.03 |
| 5,115,814 | 5/1992 | Griffith et al. | 128/662.06 |
| 5,117,831 | 6/1992 | Jang et al. | 128/662.06 |

OTHER PUBLICATIONS

"Ultrasonic Tomography Of The Heart: An Intracardia Scan Method" by Dr. Ryozo Omoto, Department of Surgery and Thoracic Surgery, University of Tokyo, Ultrasonics, Apr. 1987.

Optimized Ultrasound Imaging Catheters For Use In The Vascular System, *International Journal of Cardiac Imaging*, 1989, pp. 145–151, R. J. Crowley, P. L. von Behren, L. A. Couvillon Jr., D. E. Mai, & J. E. Abele.

Ein Weg zur intraluminaren Echoarteriographie, *Ultraschall* 8, 1989, pp. 233–236, N. Bom, C. T. Lancee, C. J. Slager, & N. de Jong.

"Early And Recent Intraluminal Ultrasound Devices", by N. Bom et al., International Journal of Cardiac Imaging, 1989.

Abstract, "Proceedings of The British Medical Ultrasound Society", The British Journal of Radiology, P. M. Handley and N. L. Browse, vol. 58, p. 689, Jul. 1985.

"The Development Of An Ultrasonic Endoscope For The Assessment Of Arterial Wall Disease", P. M. Handley, Chapters 4–8, University of London (1985).

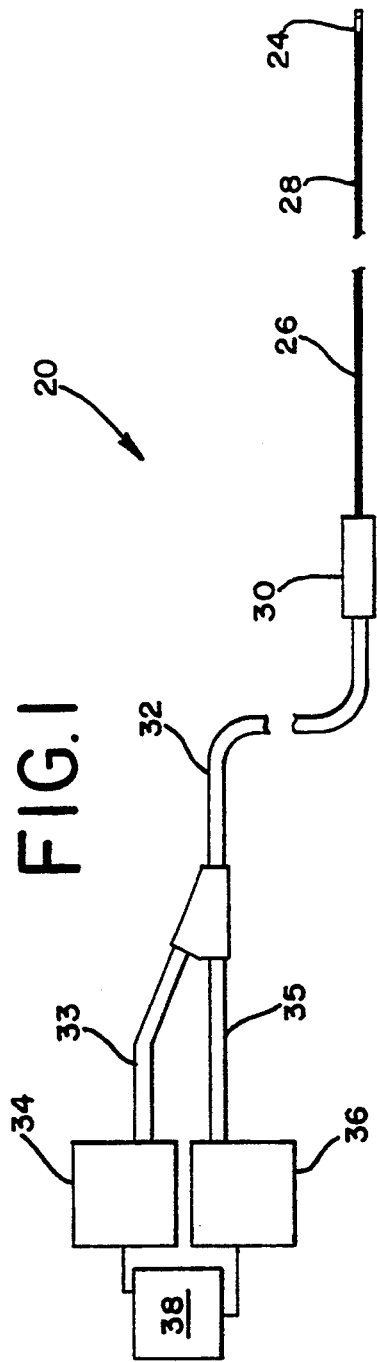
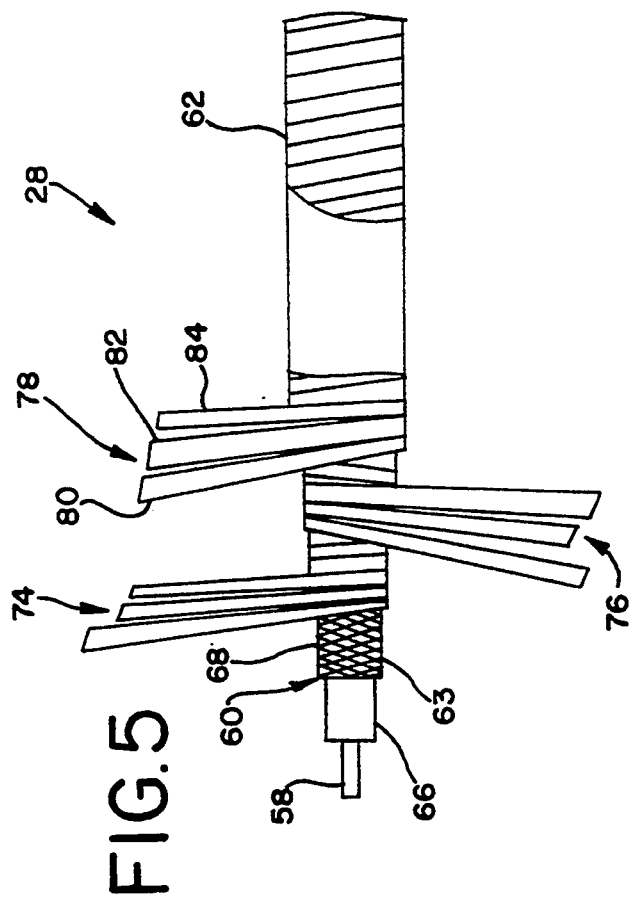

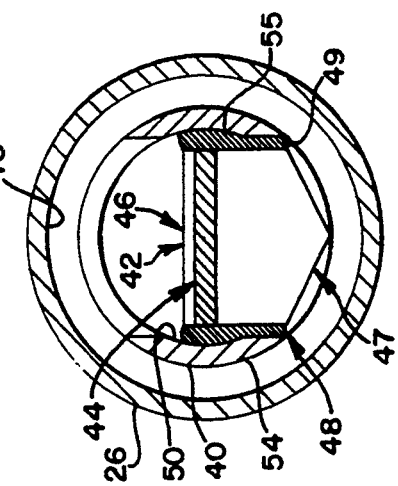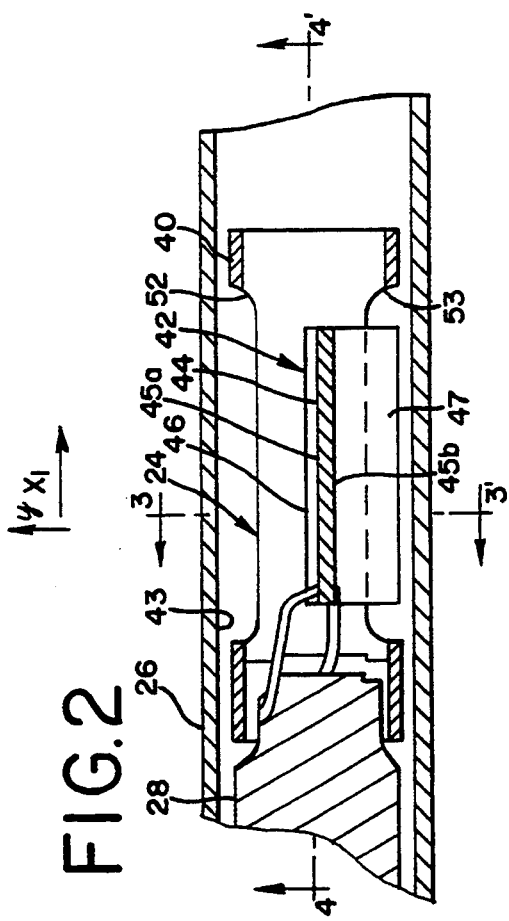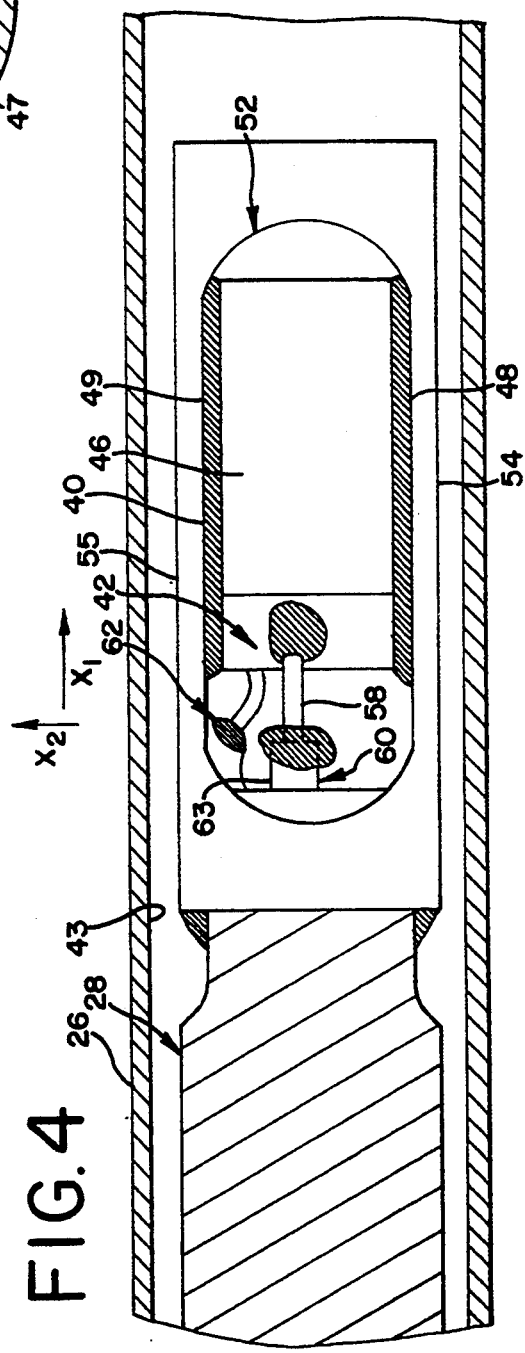

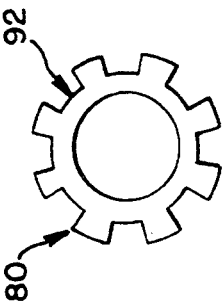
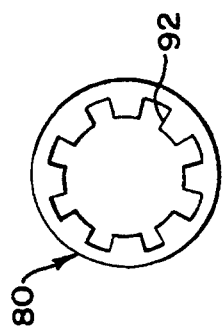
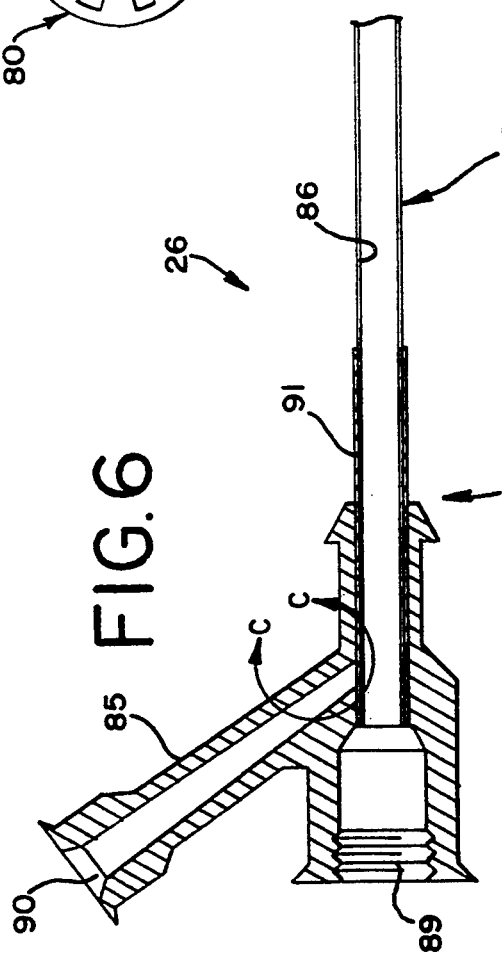
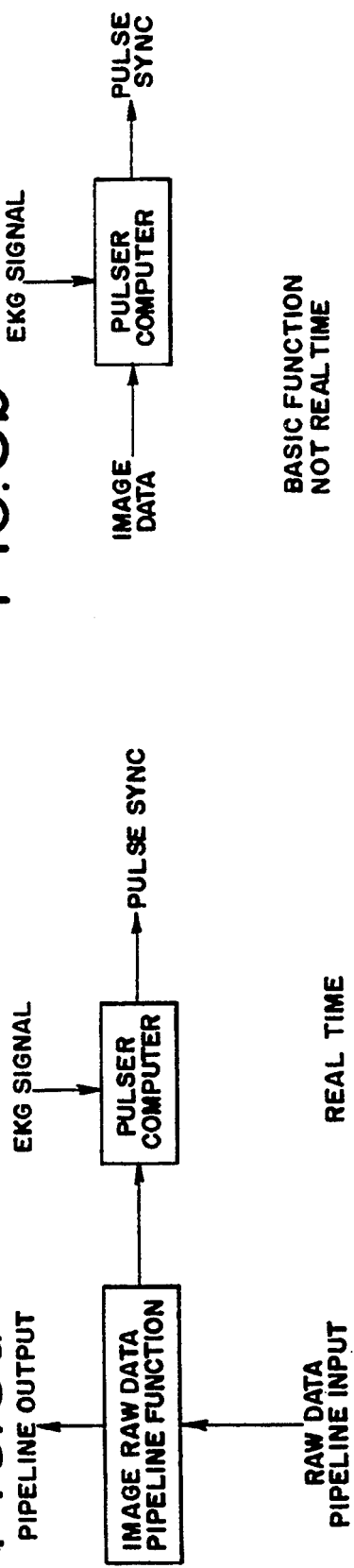

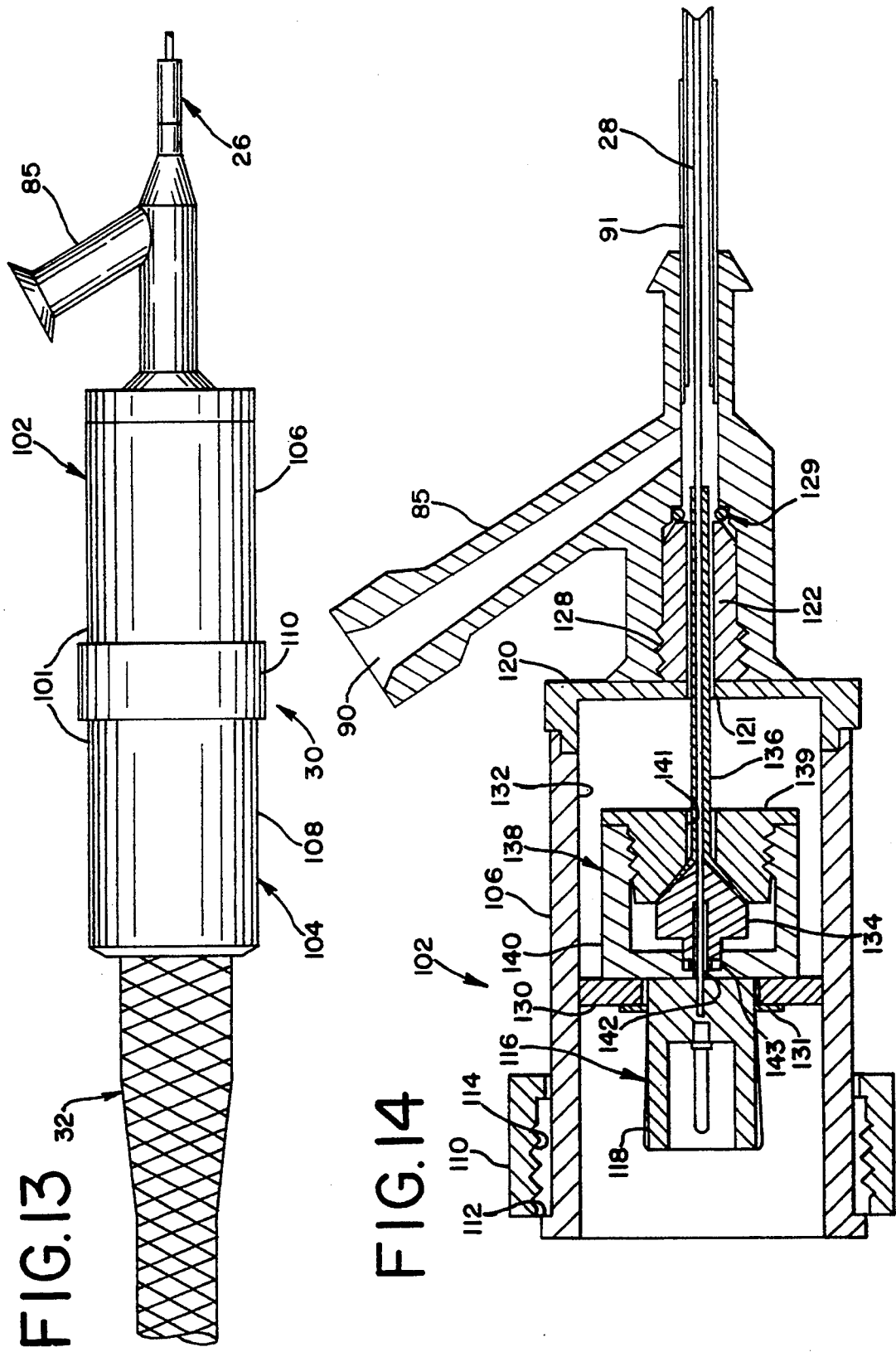

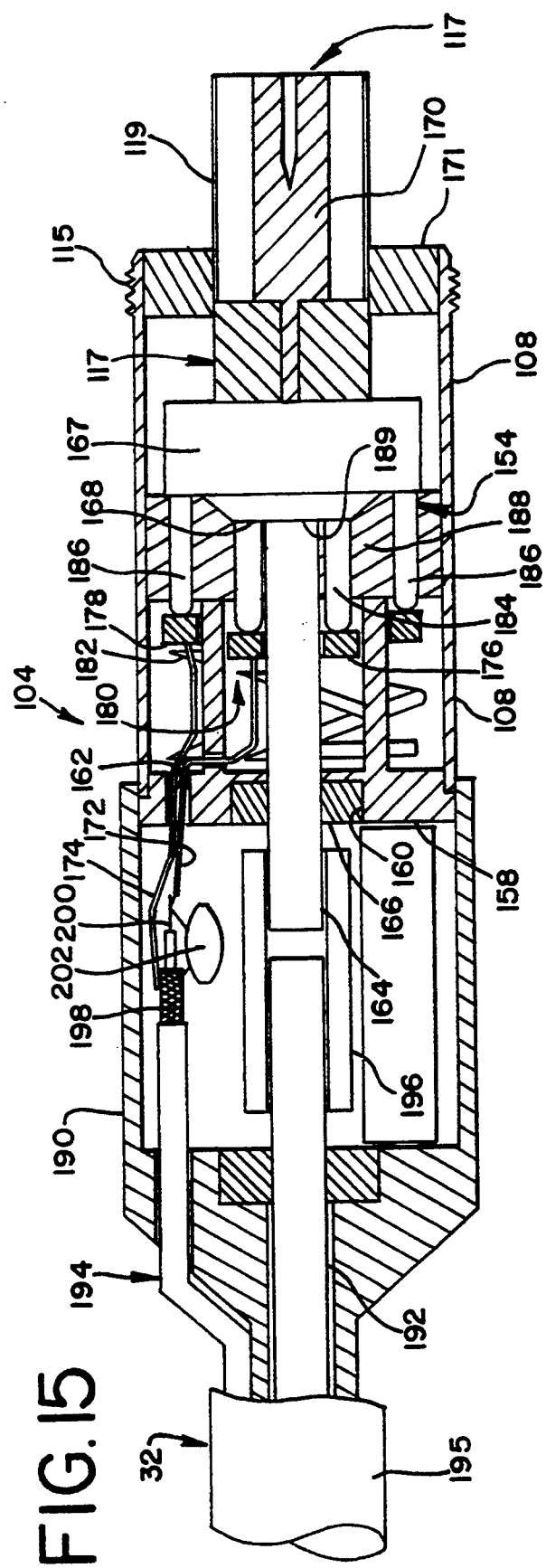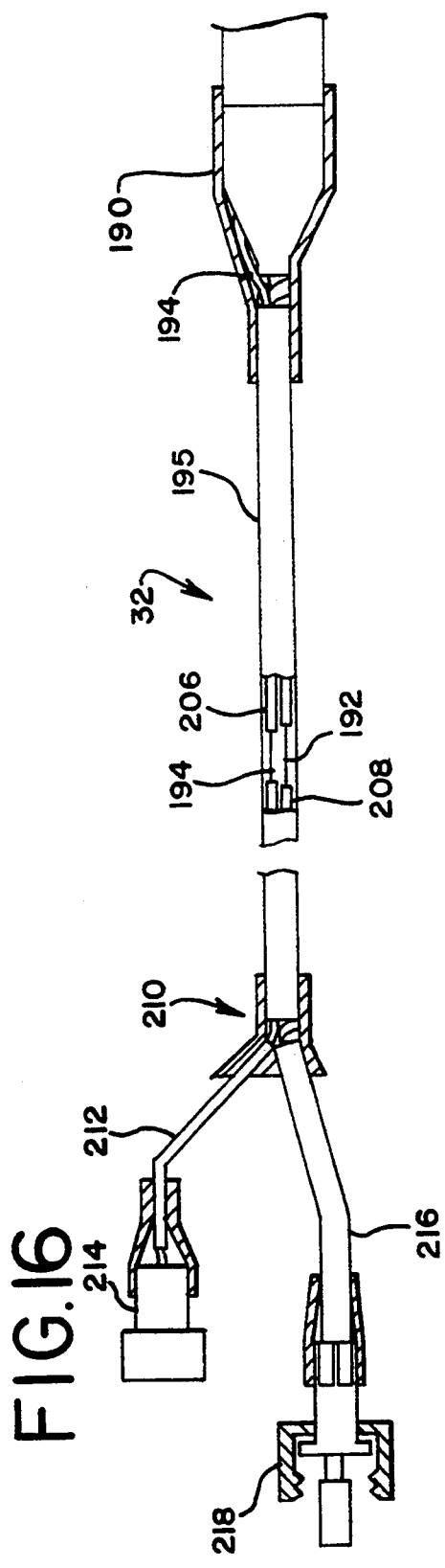

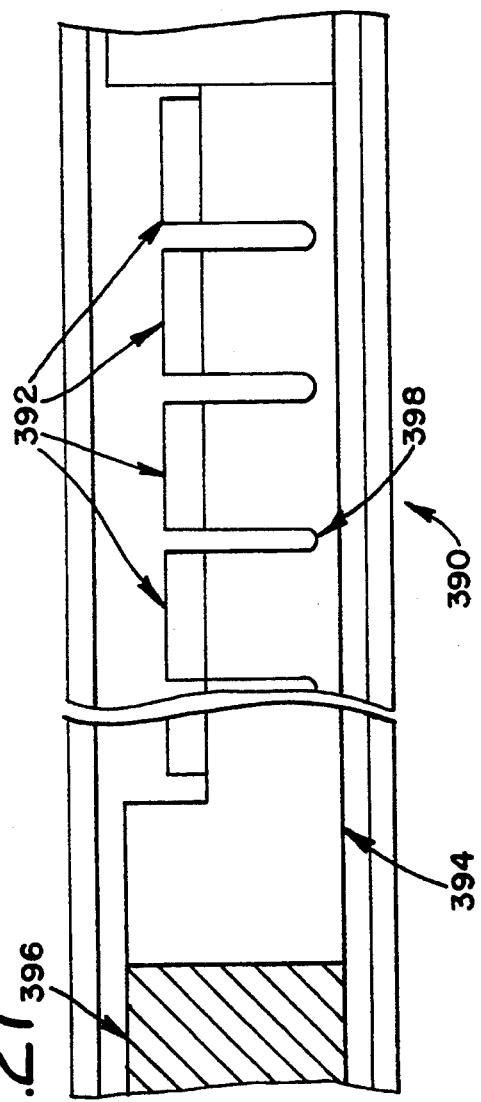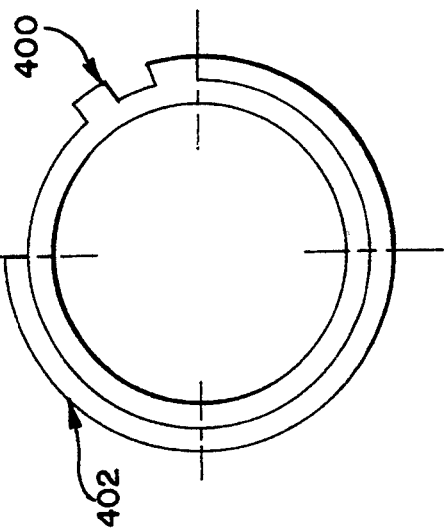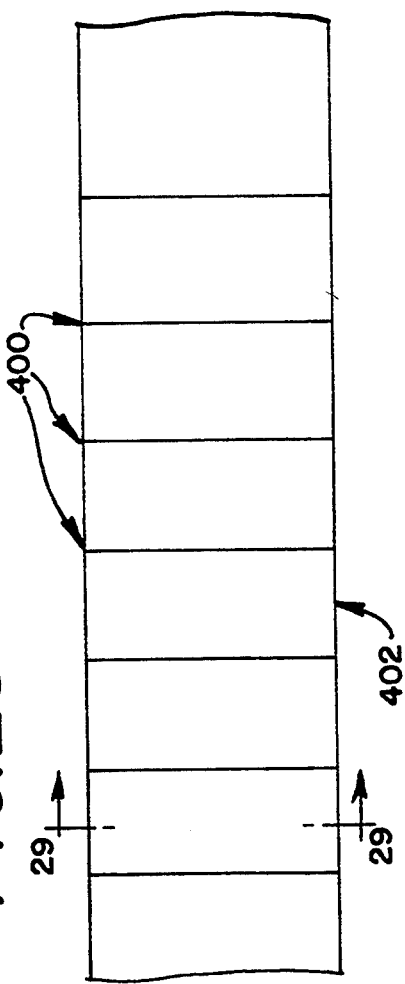

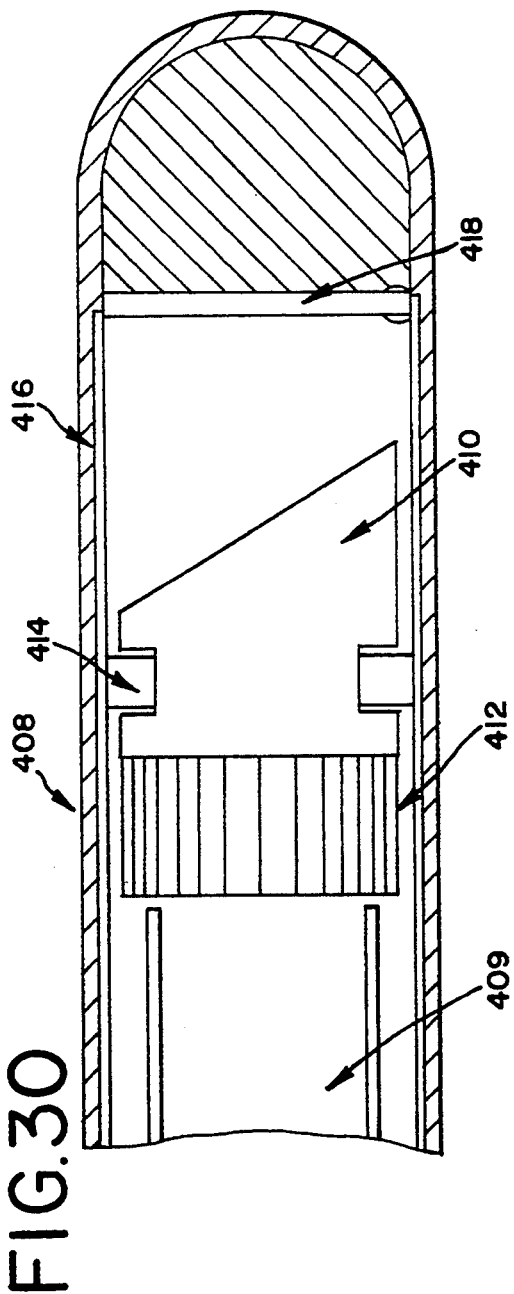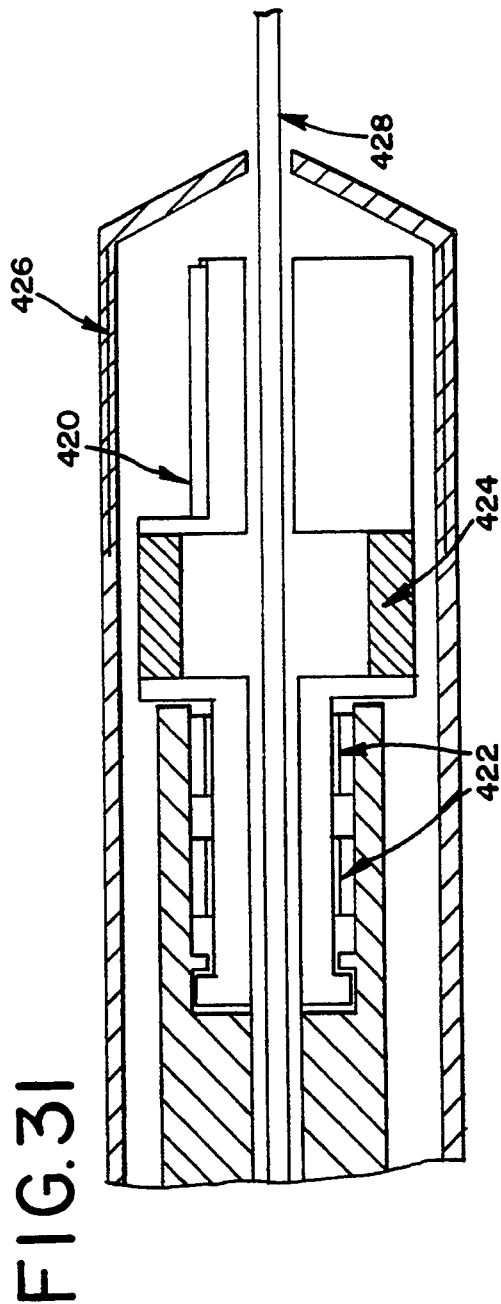

INTRAVASCULAR IMAGING APPARATUS AND METHODS FOR USE AND MANUFACTURE

This is a division of application Ser. No. 07/668,919, filed Mar. 13, 1991 now abandoned.

BACKGROUND OF THE INVENTION

This invention relates to an ultrasonic imaging device and methods for use and manufacture thereof, and particularly to an ultrasonic imaging device positionable in coronary vessels to obtain images thereof.

Ultrasonic imaging of portions of a patient's body provides a useful tool in various areas of medical practice for determining the best type and course of treatment. Imaging of the coronary vessels of a patient by ultrasonic techniques could provide physicians with valuable information about the extent of a stenosis in the patient and help in determining whether procedures such as angioplasty or atherectomy are indicated or whether more invasive procedures may be warranted. However, obtaining ultrasonic images of the distal coronary vessels with sufficiently high resolution to be valuable for making medical decisions, such as described above, requires overcoming several significant obstacles one of the most significant of which relates to the size of the ultrasonic sensing device.

Obtaining ultrasonic images of high resolution of a body organ generally requires bringing an ultrasonic sensor (i.e. a transmitter/receiver) sufficiently proximate to the organ and scanning the organ with ultrasonic pulses. Ultrasonic imaging of organs deep within the body that are surrounded by other, relatively dense organs and tissues requires connecting a sensor on a probe and positioning the sensor and the probe near or even into the organ. The heart and the vessels connected to it are organs of this type. Because it is a well known technique to insert catheters, guide wires and probes into the coronary vasculature from remote sites via arteries, such as the femoral artery, and further because some of the information of interest to the physician is the extent of stenosis on the inside walls of the coronary vessels, it would be desirable to be able to position an ultrasonic sensor connected to a probe into the distal regions of the coronary vasculature via a remote arterial site, such as the femoral artery, to obtain ultrasonic images of the coronary arterial walls.

The vessels in the distal regions of the vascular tract that would be useful to image include the coronary arteries, branch vessels stemming from the external carotid artery such as the occipital and the arteries leading to the vessels of the head and brain, splenic, and the inferior mesenteric and renal arteries leading to the organs of the thorax. To be positioned in these regions, the size of an ultrasonic sensor and probe must be relatively small not just to traverse the arterial vessel but also to avoid occluding the vessel lumen. When a device, such as a catheter, probe, or sensor, is positioned in a blood vessel, it occupies a volume which restricts blood flow within the vessel as well as in vessels proximate thereto. When a device is positioned within an arterial vessel, the blood flow through the vessel is restricted to an annular region (i.e. the area of "ring"-shaped cross section) which is effectively created between the outer perimeter of the device and the inner wall of the vessel. This would normally not present a problem in large arteries with large blood flows, such as the femoral arteries of the legs, or the aorta, or in very proximal coronary arteries. In these large arteries, any restriction caused by the device would be relatively small and the blood flow would be relatively large. However, in small arteries in remote locations, such as the occipital that leads to the brain, or the coronary arteries of sizes of 3.0 mm or less that lead to the right and left sides of the heart, any restriction of blood flow must be minimized. The consequences of occluding these small vessels can cause a loss of flow in the coronary arteries of the heart which may have several adverse effects, such as severe chest pains, or physiological changes such as arrythmia, ischemia, and tachycardiac response. These effects may be threatening to the patient and further, once begun, may be difficult to stabilize.

Moreover, not only are these latter vessels very small but these vessels are also those in which there might also be restrictive disorders, such as atherosclerosis. Atherosclerotic disease as well as other thrombus formations which occlude blood flow occurs in these smaller arteries due to the hemodynamics of the blood tissue interface. Reflecting this fact is that presently angioplasty is primarily performed in vessels of a size range of 2.0 to 3.5 mm in diameter. Such disorders would diminish the cross sectional area of these vessel lumens even more.

Therefore, a significant obstacle to using an intravascular probe device to obtain ultrasonic images of such vessels is that the probe should be sufficiently small in dimension so as not only to be positioned in these small, possibly partially occluded arteries, but also to be sufficiently small so as not to totally or almost totally occlude the lumen of the vessel into which it is positioned. Accordingly, for an ultrasonic sensor device to be used for distal coronary applications, it must be small enough to be suitably positioned in the coronary vessels and to permit a sufficient blood flow therearound. For use in the distal coronary vasculature, the exterior dimension for a sensor device should be approximately 0.040 inches (1 mm) in diameter to provide an annular region of flow in even the most distal vessels.

Ultrasonic imaging devices intended to be placed in the vascular system have been disclosed in prior patents (e.g. U.S. Pat. No. 4,794,931). However, these prior devices have had numerous drawbacks that limited their utility for the most part to uses in only the peripheral vasculature and not in deep coronary arteries. Prior devices, having diameters ranging from 3.5 French (1.2 mm) and up, would be limited by their size to only very proximal coronary arteries. Prior devices, having diameters ranging from 4.5 French (1.5 mm) and up, would be limited by their size to only very proximal locations of coronary arteries, peripheral vessels, or very proximal organ vessels. Furthermore, in addition to these limitations, prior ultrasonic probe devices have produced images lacking in sufficiently high detail and resolution to provide useful information.

There are significant obstacles to making an ultrasonic probe device with dimensions sufficiently small to fit into distal coronary vessels and yet possessing the necessary mechanical and electrical properties required for high quality ultrasonic images. For example, in order to position a probe device in a deep coronary vessel from a remote percutaneous site such as via the femoral artery, the probe device should possess a high degree of longitudinal flexibility over its length. The vessel paths of access to such deep coronary vessels, as well as the numerous branches which stem from these vessels, may be of an extremely tortuous nature. In some areas within the vascular system, an ultrasonic probe device may have to transverse several curvatures of radius of 3/16 of an inch (4.7 mm) or less. Thus, the probe device should possess a high degree of flexibility longitudinally over its length to enable it to transverse virtually any curvature of the vascular tract.

Another desired mechanical property for the probe device is stable torsional transmittance. If the device is to include a rotating ultrasonic sensor at a distal end to make radial scans of the entire cross section of the coronary artery, it should not only be flexible longitudinally, but should also be stiff torsionally. Rotation of the ultrasonic device should be achieved so that a drive shaft extending to the sensor does not experience angular deflection which might cause image distortion. Due to the continuous angular motion which dictates the location at which an ultrasound sensor scans, if angular deflection occurs at the distal end of sensor drive shaft, it can result in an artifact of angular distortion that becomes apparent on the ultrasound displayed image. This artifact can occur if the rotating sensor drive shaft experiences "whip". "Whip" may be defined as the angular deceleration and acceleration of the sensor drive shaft as a result in shaft angular deflections during rotation. As the transducer drive shaft is rotating it may undergo angular deflection if the drive shaft's torsional stiffness is low enough to make the drive shaft susceptible to dynamic changes in torsional load. It may also undergo angular deflection if the dynamic torsional loads are high and varying.

During operation, relative changes in torsional load should be minimal, therefore any induced 'whip' could be attributed to a shaft with a low torsional stiffness. The acceleration and decelerations associated with shaft whip can be described by the energy change from kinetic to potential under varying torsional load conditions. For example, as a sensor drive shaft encounters additional torsional resistance its angular velocity drops causing a deceleration and shaft angular deflection. When the shaft is free of the added resistance, the energy stored in the shaft, in the form of potential energy from the angular deflection and shaft stiffness, is released causing an angular acceleration and increase in the shaft's angular velocity.

Image quality and accuracy is dependent on constant sensor angular velocity. Image construction assumes a constant sensor velocity, therefore relative acceleration or deceleration between the expected and actual sensor angular velocity will cause image distortion.

Even if a sensor possesses the aforementioned minimal size and mechanical properties, the value of the device depends upon the quality of the ultrasonic image which in turn is a direct function of both the acoustic pulse signal and the electrical signal transmission. Therefore, in addition to the mechanical properties necessary for locating and rotating a sensor, the device should also provide a high quality electrical and acoustic signal. This may include several specific properties, such as a high signal to noise ratio of the electronic signal, impedance matching of the overall system without the need for internal electronic matching components, and minimization of voltage requirements to attain a signal of sufficient quality to provide an image.

Accordingly, it is an object of the present invention to provide a device that overcomes the limitations of the prior art and which enables the ultrasonic scanning of small diameter body vessels with a transducer probe that can be positioned therein.

It is a further object of the invention to provide an apparatus, and methods for use and manufacture, that enables obtaining ultrasonic image information of high resolution or quality.

SUMMARY OF THE INVENTION

The present invention provides a device for intravascular ultrasonic imaging, and methods for the use an manufacture thereof, comprising an elongate member with a distal end that can be positioned within a vessel of a patient's body while a proximal end is positionable outside the body. The device also includes a transducer located at a distal end of the elongate member and a signal processor connected to a proximal end of the elongate member for generating pulses to and receiving from said transducer. The device preferably includes a motor for rotating the transducer and a drive cable for connecting the transducer to the motor and the signal processor. The drive cable is operable to transmit electrical signals to and from the transducer.

BRIEF DESCRIPTION OF THE FIGURES

FIG. 1 is a schematic representation of a presently preferred embodiment of the ultrasonic imaging apparatus.

FIG. 2 is a longitudinal vertical sectional view of a distal portion of the ultrasonic imaging apparatus depicted in FIG. 1.

FIG. 3 is a sectional view of the distal portion of the ultrasonic imaging apparatus along lines 3–3' in FIG. 2.

FIG. 4 is a sectional view of the distal portion of the ultrasonic imaging apparatus along lines 4–4' in FIG. 2.

FIG. 5 is a plan view of a portion, partially disassembled, of the drive cable.

FIG. 6 is a sectional view of an embodiment of the elongate member of the system depicted in FIG. 1.

FIG. 7a a sectional view alone lines 7–7' of the embodiment of the elongate member depicted in FIG. 6 illustrating a first alternative indexing function construction.

FIG. 7b a sectional view alone lines 7–7' of the embodiment of the elongate member depicted in FIG. 6 illustrating a second alternative indexing function construction.

FIGS. 8a and 8b are block diagrams of processing steps related to acoustical indexing.

FIG. 13 is a plan view of the uncoupling member shown in FIG. 1.

FIG. 14 is a longitudinal vertical sectional view of the transducer pin assembly shown in FIG. 13.

FIG. 15 is a longitudinal vertical sectional view of the slip ring assembly shown in FIG. 13.

FIG. 16 is a plan view with a partial sectional view of the proximal drive cable shown in FIG. 1.

FIG. 21 is a diagram of signal intensity versus the position along the cross section B–B' of FIG. 18.

FIG. 27 is plan view of another embodiment of the present invention for 3-D imaging.

FIG. 28 is a view of a distal section of an alternative embodiment of the elongate member with variations represented for 3-D indexing.

FIG. 29 is a cross sectional view of the embodiment shown in FIG. 28 along lines A–A'.

FIG. 30 is a top view of a the distal end of yet another embodiment of the present invention that utilizes an alternative drive mechanism.

FIG. 31 is an alternative embodiment of that shown in FIG. 30.

DETAILED DESCRIPTION OF THE PRESENTLY PREFERRED EMBODIMENTS

I. The System

Figure 9:
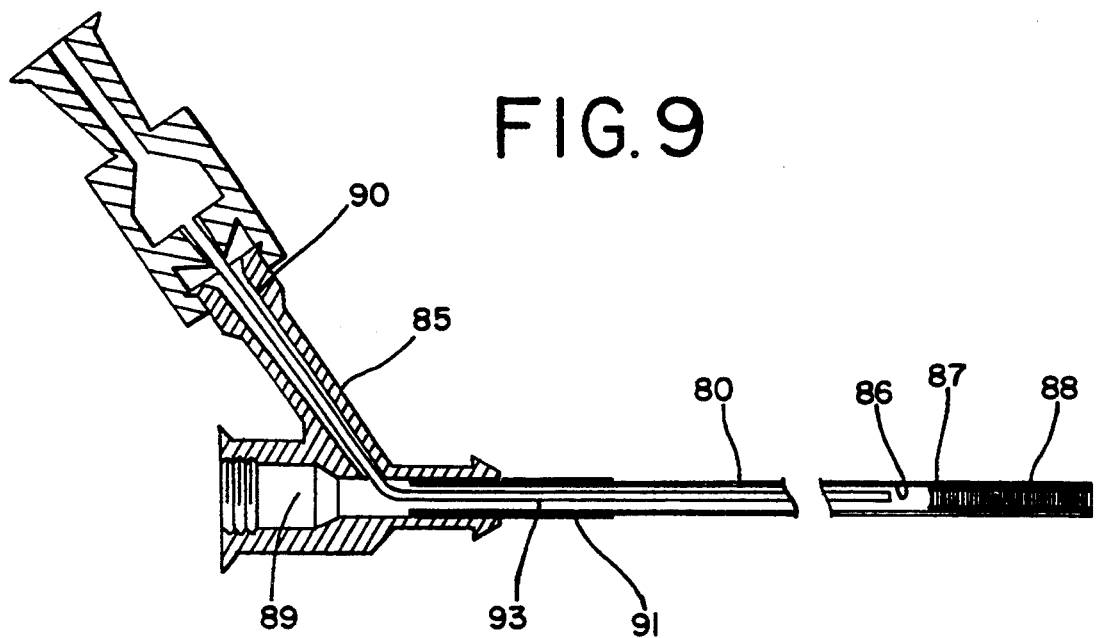
FIG. 9 is a sectional view of the alternative embodiment of the elongate member shown in FIG. 6 illustrating a first flushing method.

Referring to FIG. 1, there is depicted a schematic representation an ultrasonic imaging system 20. The system comprises a sensor assembly 24 located at a distal end of the system 20 at a distal end of an elongate member 26. The elongate member 26 can be percutaneously positioned in the cardiovascular system of a patient via a remote site such as the femoral artery so the distal end of the elongate member is located in or close to the remote site while a proximal end extends out the body of the patient. The elongate member 26 includes at a distal end thereof the sensor assembly 24. The elongate member 26 further includes means for transmitting an electrical signal between the sensor assembly 24 located at the distal end thereof and the proximal end extending out of the body of the patient. The elongate member 26 further includes means for operating the sensor assembly to make scans of the remote vessel site. In a preferred embodiment, the means for operating the sensor assembly 24 and the means for transmitting a electrical signal to and from it are provided by a distal drive cable 28 located inside the elongate member 26. The sensor assembly 24 is connected to a distal end of the distal drive cable 28. The distal drive cable 28 is connected at its proximal end to a coupling member 30 which connects to components located at a proximal end of the system 20. Specifically, the coupling member 30 serves to releasably couple the distal drive cable 28 to, and uncouple the distal drive cable 28 from, a proximal drive cable 32. The proximal drive cable 32 includes a first leg 33 that connects to a signal processing unit 34 and a second leg 35 that connects to a motor 36. Connected to both the signal processing unit 34 and the motor 36 is a control unit 38 that serves to operate the motor 36 and the signal processing unit 34. These components are described in further detail below.

This embodiment of the present invention is particularly adapted for ultrasonic diagnostic imaging in the small, distal vessels of a human patient. These vessels typically have diameters of only up to 4.5 mm diameter. In particular, the present embodiment is adapted for use in deep organ vessels where the residual diameter of the vessel may be 1.5 mm or less. However, it should be understood that embodiments of present invention may be readily adapted for use in vessels having other dimensions with corresponding advantages in these other size vessels as well. In the preferred embodiment for use in vessels having a diameter of approximately 3.5 mm with potential stenosis resulting in diameters of down to 1.2 mm, the overall maximum diameter of the distal portion of the ultrasound imaging system is preferably not more than approximately 3.2 French (1.07 mm or 0.42 inch) and preferably the distal portion of the system has an overall diameter of less than 3.0 French (1.0 mm).

In operation, the signal processing unit 34 generates electrical pulses that are transmitted to the sensor assembly 24 via a proximal electrical transmission cable inside the proximal drive cable 32 (as further described below) and the distal drive cable 28. The signal processing unit 34 also receives electrical pulses back from the sensor assembly 24 via these cables. At the same time, the motor 36 operates to rotate a proximal drive shaft located inside the proximal drive cable 32 (as described below) which in turn rotates the sensor assembly 24 to which it is coupled via the distal drive cable 28. Rotation of the sensor assembly 24 while pulsing and receiving the reflections effects an radial ultrasonic scan of the area proximate to the sensor assembly 24. In this embodiment, the motor 36 operates to rotate the transducer assembly 24 at speeds ranging from 500 to 1800 RPM, with a preferred rotational speed of approximately 1000 RPM.

The design and construction of the various components of the system are preferably computer modeled and iterated to provide optimum overall system performance. For example, for optimum performance, impedance throughout the overall system from the signal processing unit 34 to the sensor assembly 24 is carefully matched to eliminate reflections at all interfaces caused by impedance mismatch. By eliminating reflections in the system, there is a faster settling of the pulses since reflections can cause ringing of the pulse thus reducing the radial resolution. Because there is limited potential for adjustment of the impedance at the sensor assembly 24 end of the system, consistent with other requirements, the rest of the system components proximal from the sensor assembly 24 are matched to it. In this embodiment, a system impedance of 50 ohms is selected. With a system impedance of 50 ohms, readily available industry standard components, such as coaxial cables may be used for proximal equipment. A suitable sensor can be constructed and used that is matched to this impedance and that has an active surface area of 0.50 mm². Similarly, the distal drive cable 28 and the proximal drive cable 32 are constructed with an impedance of 50 ohms. The impedance of the coupling member 30 is not specifically matched to that of the rest of the system. The coupling member has a low resistance, e.g. less than 0.5 ohm. However, the length of the unmatched impedance portion of the coupling member is made to be only approximately 0.75 inch. At the preferred operating frequency of 30 Mhz, a segment of this length with an unmatched impedance can be present in the electrical transmission conductor of the system without causing a significant reflection. The signal processing unit 34 (including the pulser), at signal voltage levels, is also selected with impedance matched to the system impedance, i.e. 50 ohms, to eliminate reflections. With a matched termination at the signal processing end of the system, the signal is insensitive to the length of the cable members. This provides the advantage that the motor 36 and signal processing unit can be positioned out of the way of the physician, e.g. under a table or other convenient place.

II. The Sensor Assembly

Referring to FIG. 2, there is depicted a vertical longitudinal sectional view of a distal portion of the imaging system 20 including the sensor assembly 24 of a first presently preferred embodiment. The sensor assembly 24 is located inside the elongate member 26. The sensor assembly 24 is connected at a proximal end thereof to the drive cable 28.

The sensor assembly 24 includes a sensor housing 40 in which is mounted a transducer sensor 42. The transducer housing 40 is a hollow, generally tubular member having a cylindrical wall and open ends. The housing 40 has dimensions that provide for positioning and rotating inside of a lumen 43 of the elongate tubular member 26. In a preferred embodiment, the housing 40 has an outside diameter of 0.030 inches. This may be equal to the diameter of the drive cable 28. In a preferred embodiment, the housing 40 is a metallic tube of 304 stainless steel.

The transducer sensor operates in alternating pulsing and sensing modes. In the pulsing mode, when excited electrically, the transducer sensor 42 creates a pressure wave pulse which travels through the elongate member into the arterial environment. In the sensing mode, the transducer sensor 42 produces an electrical signal as a result of receiving pressure waves reflected back to the transducer. These reflections are generated by the pressure waves traveling through changes in density in the arterial environment being imaged. The electrical signals produced by the transducer sensor 42 are transmitted back to the signal processing unit 34 for generation of images of the arterial environment by methods known in the art and as further described below.

Referring to FIGS. 2 and 3, the transducer sensor 42 is constructed from several distinct layers including a transducer core material 44 having a first and a second metallized electrically conductive surface layers, 45a and 45b, bonded thereto, a matching layer 46, a backing layer 47 bonded to the metallized surfaces, and one or more adhesive layers. This construction provides a transducer sensor with an active area of approximately 1.0×0.5 mm. The impedance of the transducer is a linear function of the active area so for a device having an active surface area of about 1.0×0.5 mm, the impedance is approximately 50 ohm.

Transducer Sensor Core Material

In a preferred embodiment, the transducer core 44 of the tranducer sensor 42 is a flat rectangular piece of PZT (Lead Zirconate Titarate) type ceramic material. Such PZT material has an acoustic impedance of mid 20's and a speed of sound of about 5000 m/s. At this speed, the thickness for a 30 MHz sensor is about 0.003 inch. At this thickness, PZT materials should be selected with small grain sizes so that shorts are not generated during processing. The PZT material is cut to a rectangular shape of 0.5×1.25 mm. The active area after wires and a matching layer are attached is approximately 0.5×1.0 mm.

Transducer Sensor Conductive Layers

The first and second conductive layers, 45a and 45b, are positioned respectively on each face of the transducer core 44. The conductive layers 45a and 45b may be composed of a number of electrically conductive materials, such as gold, silver, copper, or nickel. However, a number of other materials, elements or alloys are suitable. Additional layers may be needed under each conductive layer to provide for adhesion to the core material, e.g., using chromium under gold. For good performance, the resistance of the conductive layers should be less than 1 ohm from one end thereof to the other.

Transducer Sensor Matching Layer

The matching layer 46 provides an impedance transformation between the transducer sensor 42 and the fluid therearound to allow a better coupling of energy into the fluid. This transformation is frequency dependent. A matching layer may be used where a difference exists between the transducer and the medium adjacent thereto. Use of a matching layer provides for a stronger and sharper pulse and thus a better image. The optimized value range for the matching layer is from 3.8 to 4.2 ($\times 10^6$ kg/m² sec.). The material that is used for the matching layer may be PVDF (Kynar) at a thickness of 0.95×(quarter wavelength thickness). The matching layer 46 is bonded to the first conductive layer 45a by means of a thin glue layer. The matching layer 46 conforms approximately in surface dimension to the active size of the transducer, i.e. 0.5×1.0 mm.

Transducer Sensor Backing Layer

Bonded to the conductive layer 45b on the opposite surface of the core 44 from the matching layer 46 is the backing layer 47. The backing layer serves to absorb acoustical energy generated off the non-imaging side of the transducer and also helps minimize energy reflections coming back to the transducer. The amount of energy traveling from the transducer core to the backing is a function of the acoustic impedance of the core and the backing material. The energy that is generated and enters the backing material should be attenuated sufficiently before it is reflected back into the core where it can distort the signal. The backing layer 47 impedance is selected to provide optimum damping so that the transducer sensor 42 vibrates for only a short duration after electrical excitation is stopped and prevents energy from being reflected to or from the artery wall to the back side of the transducer. This enables the transducer sensor 42 to be ready to receive pressure waves reflected from the arterial environment with no or minimal interference from ringing from the pulse. The impedance of the backing layer may be determined by computer modeling and in this embodiment is selected in the range from 5 to 7 ($\times 10^6$ kg/m$^2$ sec.). The composition used for the backing is preferably a tungsten and silicon rubber mixture. The acoustical impedance of the mixture can be varied by mixing various sized tungsten powder particles into the silicon rubber. This mixture is very good for backing since it has very high attenuation. The backing layer 47 may be bonded to the conductive surface 45b by means of a thin glue layer applied on backing type material.

The backing layer 47 conforms in surface dimension to the size of the active area, i.e. approximately 0.5 × 1.0 mm. In order to allow sufficient ringdown after pulsing, the backing layer 47 is preferably provided with a maximum thickness, or depth dimension, consistent with the dimensions of the sensor housing 40, drive cable, elongate member, etc. As shown in FIG. 3, in the present embodiment, the backing layer 47 may be made to a dimension equal to the cross-section of the drive cable 28 and/or housing 40. This allows for a backing layer of a maximum size to provide for sensor ringdown time and yet is small enough to fit deep into the coronary arterial environment. The backing layer may be approximately 0.012 inches in thickness.

The transducer sensor 42 is connected by the sides 48 and 49 thereof to the interior of wall 50 of the housing 40. The transducer sensor 42 is mounted so that the central axis of the sensor assembly 24 passes through or is close to the plane defined by the flat surface of the transducer sensor 42. Thus, the flat surface of the transducer faces perpendicular to its axis of rotation. This permits maximizing the dimensions of the matching layer and backing layer. This construction also allows for secure mounting of the sensor assembly 24 to the drive cable 28 by inserting and connecting the housing 40 to the distal end of the drive cable 28.

The housing 40 has a first acoustic window (or aperture) 52 and a second window 53 oppositely located from each other in the cylindrical wall of the housing 40. These windows are preferably approximately rectangular in shape having parallel sides in the longitudinal direction of the housing 40 and rounded sides in the chordal direction. These windows may be formed by removing portions of the material of the cylindrical wall of the housing but leaving narrow bands 54 and 55 of the wall 50 of the housing 40 onto which the transducer sides 48 and 49 may be bonded. In a preferred embodiment, both windows 52 and 53 are approximately 0.6 × 2.0 mm. In the sensor assembly 24, the transducer sensor 42 is mounted and located in the housing 40 directly facing the first window 52 so that the ultrasonic signal is emitted from the transducer sensor 42 through the first window 52.

The size and geometry of the windows are related to the pulse generating characteristics and the advantages of the disclosed window geometry are described below in conjunction with the description of the operation of the pulser.

These windows 52 and 53 may also be useful during the construction and testing of the sensor assembly 24. The sensor assembly 24 can be constructed and tested before mounting to the drive cable 28 by connecting the wires between the tested sensor and the tested cable inside the window. This ability to screen sensor assemblies prior to attachment to the drive cable increases transducer drive shaft assembly yield dramatically. Also, the housing design also allows alignment of the transducer in the elongate member during rotation by the smooth rounded end and fit between elongate member 26 and the housing 40.

Referring to FIG. 4, the sensor assembly 24 is connected at its proximal end to the distal end of the drive cable 28. Specifically, the first conductive layer 45a of the transducer sensor 42 is connected to the distal end of an internal conductor 58 of the drive cable core wire 60. A distal end of an external layered coil portion 62 of the drive cable 28 is connected to the housing 40. These connections may be made by means of an epoxy adhesive. An external conductor 63 (also referred to as the reference plane conductor) of the core wire 60 is sealed by means of an epoxy. The reference plane conductor 63 of the core wire 60 is connected electrically to the housing 40 via the external layered coil portion 62 of the drive cable 28.

In a preferred embodiment, a single transducer is mounted in a single transducer housing which is connected at the distal end of a drive cable. However, in other embodiments, as described below, more than one transducer with one or more housings, may be connected serially at the end of a drive cable in order to make scans of a length of a vessel. In such multi-transducer embodiments, an appropriate switching device may be utilized in conjunction with the signal processing unit and the transducers to coordinate pulsing and receiving data.

III. Drive Cable

Referring to FIG. 5, there is depicted a portion of the drive cable 28, partially disassembled. In the assembled imaging system 20, the drive cable 28 is positioned inside the elongate member 26 and is connected to the sensor assembly 24, as described above. The drive cable 28 serves as both the mechanical and electrical link to the sensor assembly 24.

The drive cable 28 conducts the electrical signal from the proximally located signal processing unit 34 (via the proximal drive cable 32) to the sensor assembly 24 and conveys the sensed signal from the sensor assembly 24 back to the signal processing unit 34. In order to provide a drive cable of a suitably minimal dimension for coronary applications while providing both the necessary mechanical and electrical properties, the electrical components of the drive cable provide for mechanical motion transmittance as well. Thus, the drive cable 28 connects the sensor assembly 24 to the proximally located motor 36, via a drive shaft located in the proximal drive cable 32, in order to rotate the sensor assembly 24 to scan the coronary vasculature with an ultrasonic signal.

In order to provide high quality electrical signal transmission, the drive cable 28 possesses a controlled matched impedance, a low signal loss, and high shielding and conductivity at high frequencies. As mentioned above, the need for a matched impedance in the drive cable 28 follows from the requirement for matching impedances at interfaces of the overall imaging system from the signal processing unit 34 to the sensor assembly 24 in order to eliminate reflections. Because of the relative difficulty in adjusting the impedance at the sensor assembly 24 end of the system, the rest of the system components, including the drive cable 28, are matched to that of the impedance of the transducer sensor 42. Accordingly, the impedance of the drive cable 28 is matched to that of the sensor assembly 24 and in this embodiment is established to be 50 ohms.

Mechanically, the drive cable 28 possesses high torsional stiffness (i.e. minimal angular deflection under operating torsional load) yet possess longitudinal (axial) flexibility to allow percutaneous positioning in the coronary vessels. In addition, as mentioned above, the drive cable 28 also possesses dimensional properties suitable for positioning in a patient's coronary vasculature, specifically the drive cable 28 has a low profile diameter to navigate torturous coronary arteries. A present embodiment provides these features in part by a coaxial multi-layer drive cable construction. The drive cable 28 includes a core wire 60 located inside of an outer layered coil assembly 62, as explained below.

The core wire 60 is located at the center of the drive cable 28. The core wire 60 includes an insulated internal conductor 58. The core wire 60 has a diameter of 0.014 inch and its internal conductor 58 is 38 AWG (7 strands of 46 AWG) copper wire. The internal conductor 58 is surrounded by a teflon coating that forms an insulator layer 66. Teflon is used as an insulator for the internal conductor 58 of the core wire 60 because of the relatively low dielectric constant which allows for a smaller cable, less loss, and higher speed of electrical transmission for a given impedance.

Around the insulated internal conductor 58 is an external conductor 63 in the form of a braided shield which forms the exterior electrical shield of the core wire 60. The braided shield is preferably composed of eight silver-plated, rectangular copper strands 70, four in each direction of rotation. Specifically, each strand is 0.001×0.007 inch oxygen free highly conductive (OFHC) copper with 50 microinches of silver plating.

Use of flat wire of these dimensions for the construction of the braided shield allows excellent coverage of the core wire 60 while maintaining a low braid profile. This flat wire braid contributes only about 0.004 inch to the overall cross-section of the drive cable 28. Furthermore, the 7 mill cross-sectional area of each strand provides enough strength to form the braid with standard braiding equipment. The use of flat wire for the braided shield of the external conductive wire 63 also provides advantages for electrical transmission through the drive cable 28. A flat wire braided shield with its inherently large surface area produces a conductor of low resistance (i.e. low cable loss) when compared to dimensionally equivalent round wire braided shields. Because electrical current travel through a braided shield following a path of least resistance, the use of a rectangular braid for the shield provides a large surface area at overlapping wires allowing lower resistance contacts thereat.

Use of silver plating on the external conductive wire 63 provides several further advantages. First of all, the silver plating provides a high quality environmental seal from corrosion. In addition, the silver plating on the flat copper wires of the braided shield of the external conductive wire 63 also advantageously reduces the shield's electrical resistance at the high electrical frequencies due to "skin effect". Electrical transmission through a conductor wire at high frequencies exhibits a "skin effect" which is a phenomena wherein the electrical current tends to increasingly travel in the outer periphery of a conductor as the signal frequency is increased. At the frequencies of operation of the imaging system, most of the current would be carried in the conductor within less than 0.0005 inch of the surface of the conductor. This is one of the reasons that the external conductor wire 63 is made with silver plating because silver has a lower resistivity than copper. For a given thickness more current will be carried in a silver layer than in the copper base.

A further reason for using silver plating is its property of non-corrosiveness which helps maintain low electrical resistance at the overlapping joints of the braided shield of the external conductor 63. The application of the silver plated, braided shield to the insulated internal wire thus forms a high quality miniature 50 ohm coaxial cable with a total diameter less than 0.030 inch (0.75 mm).

In the drive cable 28, around the core wire 60 is located the layered coil assembly 62. In a preferred embodiment, the layered coil assembly 62 comprises a multi-layer, multi-strand coil for optimum torque transmittance. The layered coil assembly 62 of the present embodiment is comprised of three layers 74, 76, and 78. Each coil layer is composed of three separate wires strands, e.g. coil layer 78 is comprised of strands 80, 82, and 84. Each strand may be comprised of a 50 microinch silver plated, oxygen free highly conductive (OFHC) copper ribbon wire having dimensions of 0.001×0.007 inch. This construction of the layered coil assembly provides for suitable torque transmission (or stiffness) by reducing the torsional load per strand.

These three layers 74, 76, and 78 are applied in opposing winding directions to the layer immediately adjacent thereto. For example, coil layer 74 is wound in an opposite helical direction from that of coil layer 76, and coil layer 76 is wound in an opposite helical direction from that of coil layer 78 (but coil layer 78 would be wound in the same helical direction as coil layer 74). The coil winding direction is determined so as to be consistent with the direction of drive cable rotation so that during operation of the system, the layered coil assembly will tend to tighten upon itself thereby providing additional torsional stiffening effects to the drive cable during operation without decreasing the cable's longitudinal flexibility during positioning. Increasing the torque stiffness reduces the angular deflection per coil layer.

Again, the use of flat wire for the layered coil assembly has several advantages. Using flat wire helps in maintaining the low profile of the drive cable, e.g only approximately 0.026 inch. This is significantly smaller than would be possible if a round wire of equivalent inertial moment were used. In addition, the use of multiple flat wire coils provides a significant amount of shaft flexibility due to the inherent slip planes between coils and strands which facilitates placement of the drive cable in the coronary arteries.

The utilization of silver plated OFHC copper for the layered coil assembly 62 advantageously benefits the drive cable's electrical properties as well. The use of the silver plated OFHC copper provides shielding effectiveness and lower resistance than other conductors (both DC resistance and high frequency resistance due to "skin effect" in conductors). These properties reduce the electrical signal attenuation through the drive cable 28 and aid in producing the cable's matched impedance. These electrical characteristics improve the overall system performance by improving the signal to noise ratio and eliminating the need for impedance matching components.

Manufacturing Process for the drive cable

The drive cable 28 may be constructed according to the following procedure.

First, the core wire 60 is constructed. The braided shield for the reference plane conductor is constructed over a 0.014 inch diameter teflon insulated core wire using a Kokubun braiding machine. The Kokubun braider utilizes 16 bobbins containing braid wire moving in a inter-twining planetary action to create an interlaced braid. Bobbin movement, in terms of orbiting speed, and feed rate of the central core wire through the braiding area are controlled by two speed regulated motors, such as 2¼ H. P. Emerson Motors, P/N 3120-406. Motor speed of the core wire take up pulley and the bobbin rotation are closely regulated to predetermined values to ensure finished shaft's mechanical and electrical properties. This may be done with a Focus 1 Speed Controller.

The following process is followed to set up the Kokubun braiding machine. The teflon insulated internal wire 58 is routed through the center guide of the braider's bobbin carriage. Due to the fragility of the internal wire and the ribbon wire to be braided over it, an additional core wire guiding apparatus providing wire support, back tension, and braid wire entrance angle guiding is added to the Kokubun braiding machine. Also, the back tension provided at the bobbins for the braid flat wire has been reduced to approximately 35% of its original value. A modified upper guide has been added to control the small diameter braided wire's movement during the braiding process.

The Kokubun braider provides positions for 16 bobbins from which to create a 16 strand braid. Eight of these bobbins are removed to generate a coarser braid. The eight bobbins removed consist of 4 in each direction in an alternating fashion such that the remaining interleaved braid consists of four strands in each direction.

The braiding machine is started and bobbin carriage and braid take up wheel motor speed are adjusted. The bobbin carriage speed is set to 395±5 RPM. The braid take up wheel speed is set to 530±5 RPM. The braider configuration is modified such that the bobbin carriage motor has been fitted with a 5:1 gear reducer and similarly, the braid take up wheel motor utilizes a 30:1 gear reducer to provide the appropriate carriage and take up speeds.

The internal wire is routed through the braider's main guide and the upper broad guide and attached securely to the take up wheel.

Bobbins containing the 0.001 inch×0.007 inch silver plated OFHC copper ribbon wire are threaded through the upper guide and attached to the braider's take up wheel, one strand at a time. Using the manual carriage crank, the bobbin carriage is rotated through 5 full rotations in order to initiate the braid on the internal wire.

After initiation of the braid onto the internal wire, the braid is bonded to the core wire using a cyanoacrylate adhesive over the entire existing braid length.

The braiding machine is started by simultaneously switching on both the carriage motor and the take up wheel motor. The motor speeds are verified with respect to their preset values. The braider is then allowed to operate for sufficient time to produce the required length of braided core cable based on the braider's approximate production of 0.33 feet/min.

Upon completion of the braided length, the braid is bonded using a cyanoacrylate adhesive over 0.5 inch bond length. The braid is cut at the bond area and removed from the braiding machine. The core wire portion is completed.

Next, the layered coil portion 63 is added to the core wire 60. A length of core wire of 66 inches is provided. The core wire 60 is prepared for the addition of the layered coil portion 62 by bonding the braided wire ends of the external conductor 63 using cyanoacrylate adhesive over a 0.5 inch length to prevent unravel of the braid.

The application of layered coil portion 62 to the core wire 60 is performed using an Accuwinder Model CW-16A. The core wire is loaded in to the coil winder head and tail stock chucks. Three spools of 0.001 inch×0.007 inch silver plated, OFHC copper ribbon wire are loaded on the coil winder's spool carriage. The wires are individually threaded through the coil winder's two guides and two tensioning clamps and finally through the three wire, lead angle guide. Wires must be routed under the three wire guide wheel and over the lead angle guide. The tensioning clamps are set to light tension. The spool carriage is moved into its initial coiling position; it is located such that the lead angle wire guide is approximately 0.25 inches (axially) from and head stock, and approximately 0.005 inches (radially) from the core wire. Guide adjustments are made by loosening their retaining screws.

The first multistrand coil 74 is wound with the coil winder's rotation direction switch in the clockwise (CW) position. This coil winding rotation direction requires the three coil strands to be routed beneath the core wire and secured to the head stock spindle.

The coil winding computer controller is powered on in conjunction with the coil winder itself. Control by the computer over the coil winder is obtained by initiating the following winding parameters via the winding program ULTRA_SD: coil pitch=0.0232 inches, maximum winding speed=1780 RPM. The lead angle at which the wire approaches the core wire is controlled by way of the lead angle guide and the coil pitch. The winding control program is down loaded to the coil winder.

Axial tension is slowly added to the core wire until a value of 0.3 to 0.5 pounds-force is reached.

The operating lever is lowered. Using the speed control knob, the coil winding speed is slowly increased to a maximum value of 60%. Core wire tension is continuously monitored during the coil winding process to maintain a wire tension of 0.3–0.5 pounds-force.

Coil winding is continued until the lead angle guide is within 1 inch, axially, of the tail stock chuck. The coiling process is halted by raising the operating lever and reducing the speed control to 0%. The coils are bonded to the core wire at the head and tail stock location over a 0.5 inch bond length. The three strands used to form the coil 74 are cut at the core wire 60 and care is taken to prevent damage to the core wire 60. The spool carriage is returned to the head stock location in preparation for applying the second, opposing, coil 76.

The tail stock pulley is loosened such that it can move independently of the coil winder drive shaft. The tail stock spindle is rotated 5 full revolutions in the CCW direction (when viewing the front of the tail stock chuck) in order to preload the first coil. The tail stock pulley is tightened.

The three ribbon wires to be coiled are routed under the three wire guide, over the lead angle guide, and placed over the core wire; the wires are temporarily secured to the head stock spindle. The coil winder's rotation direction switch is moved to the Counter Clock Wise (CCW) position. The operating lever is lowered and the speed control is increased gradually to 60%. The core wire tension is maintained at 0.3–0.5 pounds-force.

Coiling is continued until the lead angle guide is within 1 foot, axially, of the tail stock chuck. The coiling process is halted by raising the operating lever and reducing the speed control to 0%. The coils in this layer 76 are bonded to the core wire 60 at the head and tail stock locations over a 0.5 inch bond length. The three strands used to form the coil 76 are cut at the core wire 60 and care is taken to prevent damage to the core wire 60. The spool carriage is returned to the head stock location in preparation for applying the third coil 78.

The tail stock pulley is loosened such that it can move independently of the coil winder drive shaft. The tail stock spindle is rotated 5 full revolutions in the CW direction (when viewing the front of the tail stock chuck) in order to preload the second coil. The tail stock pulley is tightened.

Ribbon wires to be coiled are routed under the three wire guide, over the lead guide, and placed under the core wire; the wires are temporarily secured to the head stock spindle. The coil winder's rotation direction switch is moved to the Clock Wise (CW) position. The operating lever is lowered and the speed control is increased gradually to 60%. The core wire tension is maintained at 0.3–0.5 pounds-force.

Coiling is continued until the lead angle guide is within 1 foot, axially, of the tail stock chuck. The coiling process is halted by raising the operating lever and reducing the speed control to 0%. The coils are bonded to the core wire at the head and tail stock locations over a 0.5 inch bond length. The three strands used to form the coil 78 are cut at the core wire 60 and again care is taken to prevent damage to the core wire 60. The spool carriage is returned to the head stock location.

Exiting the coil winding computer control program is accomplished by pressing the escape key (esc) at the computer keyboard, lowering the operating lever, and gradually raising the speed control above 0%. This sequence will create a user prompt to continue or exit to the main menu. A "M" is keyed to return the user to the main menu.

The completed drive cable 28 is removed from the coil winder. The remaining coil strands at the head stock are removed by trimming.

Utilizing the above described method, a preferred embodiment of the drive cable 28 is provided having an impedance of 50 ohms, a low electrical signal loss of 10–12%, and high shield and signal conductivity at high frequencies in the range of 10–50 MHz (which includes the preferred operating frequency of 30 Mhz). A cable constructed according to the above described method can possess a relatively low loss, from 0.9 to 1.4 Db loss over the required frequency range. In the preferred embodiment, the drive cable 28 has a diameter of 0.028 inch which is suitable for use inside a lumen of the elongate member 26 having an internal diameter of approximately 0.035 inches.

IV. The Sheath

As mentioned above, during operation of the intravascular imaging system 20, the drive cable 28 and sensor assembly 24 rotate at an angular speed while the transducer sensor 42 is excited and monitored. In order to accommodate this rotation in the human body, the drive cable 28 and sensor assembly 24 are located in the flexible elongate member 26. The elongate member 26 is composed of a non-rotating, bio-compatible sheath that not only encloses both the drive cable 28 and sensor assembly 24 but also serves to position the transducer sensor 42 at a desired location in the coronary vasculature. Referring to FIG. 6, in the preferred embodiment, the elongate member 26 comprises a tubular sheath 80 having a distal portion 82 that can be positioned in a coronary artery and a proximal portion 84 that extends out of the body of the patient. The proximal portion 84 of the sheath 80 is fixed to a stationary (non-rotating) component, specifically to a catheter manifold 85 which in turn is connected to the housing of the uncoupling member 30 (as described below and as depicted in FIG. 14). As shown in FIGS. 1, 2, and 4, the sensor assembly 24 is located in a lumen of the elongate member 26 and specifically in a lumen 86 of the sheath 80 in a distal portion thereof.

In order to permit the transmission of the ultrasonic signal from the transducer sensor 42 which is inside of the sheath 80 into the body of the patient (and the reflections back again), the sheath 80, or at least a distal portion thereof, is made of a material that is transparent to the ultrasonic signal. In the present embodiment, the sheath 80 or the distal portion thereof is made of a TPX material, specifically a methylpentene copolymer plastic. The TPX material has an acoustic impedance close to water, a low coefficient of friction, and good mechanical properties. Because the acoustic impedance of the TPX material is close to water, very minimal signal reflections are created at the sheath/blood interface. This characteristic allows the TPX material to appear transparent to the transducer.

The sheath 80 is formed having a low profile suitable for positioning in the coronary vasculature. In a preferred embodiment, the sheath has 80 an external diameter of 0.040 inch. The TPX material lends itself easily to the extrusion process and can be readily drawn to very thin wall diameters. In this embodiment, the wall diameter of the sheath is 0.0025 and the diameter of inner lumen is 0.035.

In addition to providing a non-rotating interface to the body, the sheath 80 furnishes other features. Because the TPX material has a low coefficient of friction, it provides a low frictional resistance bearing surface between the internal drive cable 28 and the wall of the lumen 86 of the sheath 80.

In addition, the sheath 80 provides mechanical support to the drive cable 28 in order to develop good "pushability" for cable manipulation. The TPX material possesses good mechanical properties for an extruded copolymer. The mechanical strength of the TPX material coupled with the axial stiffness of the drive cable 28 generates a sufficient degree of "pushability", i.e. structural support in the sheath assembly, for positioning the sensor assembly 24 in coronary arteries.

Located in the lumen 86 of the sheath 80 near the distal end is an inner lumen seal 87. This inner lumen seal 87 serves to establish a barrier between the interior of the sheath 80 and the patient's blood vessel. This shields the blood vessel from the turbulence caused by the rotation of the drive cable 28 and sensor assembly 24. When the sensor assembly 24 is positioned in the sheath 80, the distal end of the sensor assembly 24 is approximately 0.050 inches from the inner lumen seal 87.

At a distal end of the sheath 80 is a guiding tip 88. The guiding tip 88 may be located in the lumen 86 of the sheath 80 distally from the inner lumen seal 87. The guiding tip 88 may be comprised of a radiopaque material, such as a coil of thin platinum wire. Platinum, with its inherent radiopacity, wound in a coil configuration produces a soft, flexible, radio-opaque, crush resistant tip. Mounting the coil inside the lumen 86 of the sheath 80 permits retaining the smooth outer surface of the sheath 80 thereby facilitating maneuvering the sheath 80 through a guiding catheter and eventually into a coronary artery.

As mentioned above, at a proximal end of the sheath 80 is located the catheter manifold 85. The catheter manifold 85 has a first or main port 89 generally aligned and communicating with the lumen 86 of the sheath 80 and a second port 90 also communicating with the lumen 86 of the sheath 80. A strain relief coil 91 is located around the outside of the proximal end of the sheath 80 and extends into and is bonded between the sheath 80 and the catheter manifold 85. The catheter manifold 85 is utilized to connect the sheath 80 to the uncoupling member 30, as described below. The drive cable 28 is installed into the sheath 80 via the main port 89. The second port 90 may be used for flushing of the sheath 80, as described below.

The sheath 80 may also provide for a means of rotational compensation in order to continuously calibrate the transducer's angular orientation during operation. One of the drawbacks associated with rotating ultrasonic imaging devices is angular distortion between the encoders at the proximal end and the sensor at the distal tip of the catheter. There are two main types of the distortions, those changing in time and those fixed to the phase of revolution. The fixed distortion is caused by friction or stiffness that causes a repeatable torque variation with each cycle. This can be found in almost every rotating element to some degree. The distortion that changes in time causes the image to rotate periodically. The major source of this is the heart moving, which flexes the elongate member causing a frictional torque variation synchronous with the heart beat.

The present embodiment provides a solution to this problem by means of an acoustical indexer. An acoustical indexer is a locational marking that is put on, or built into the sheath to provide a rotational registration. This registration is constructed in the manner so that it can be readily identified in the signal processing.

Referring to FIGS. 7a and 7b, rotational compensation markers 92 can be incorporated circumferentially in the wall of sheath 80 in a distal portion thereof. The markers 92 may be splines or patterns incorporated on the interior surface of the sheath 80, as depicted in FIG. 7a, or on the exterior surface of the sheath, as depicted in FIG. 7b. Preferably, the markers 92 are located at periodic positions 45 degree from each other around the circumference of the sheath wall. The markers 92 can be made from a variable thickness in the sheath material, but could be made from two different materials. These markers 92 may be formed in the extruding process for the sheath and may be made just in the region of the sensor or may extend over the entire length of the sheath. Each wall thickness change may be recognized by the signal processing unit 34 and can be used to verify the transducer's angular position during operation. The thickness steps could be made at various ramp rates. With a pattern in the sheath wall, the signal processing unit can follow the image variation in distance. By following and holding steady one edge or feature, the time variable distortion is corrected. This compensation ability removes any discrepancy in a image due to an angular speed change of the transducer.

By using a pattern of acoustic indexing markers as shown in FIGS. 7a or 7b where the thickness is varied every 45 degrees, fixed distortions can be corrected. Periodically, the data of the image representing the sheath would be analyzed to determine the correct time spacing of the triggers. This data is transferred to the pulser that has a variable time spaced pulse capability. By using a 1000 pulse per revolution encoder connected to the motor that provides the synchronizing of the motor to the pulser, there is more than enough resolution to generate the required pattern. The screen is divided up into 200 pie shaped angular divisions, each of these divisions is called a vector. For a 200 vector screen, the pulser needs to generate 200 pulses per revolution by dividing up the 1000 pulses into the required spacings.

A block diagram of the indexing data processing is shown in FIGS. 8a and 8b. A real time configuration tracks an edge in real time and adjusts the pulse pattern very quickly, as represented in FIG. 8a. The data is intercepted from the raw data pipeline, processed and transferred to the pulser computer. The EKG signal would be useful for calibrating the image to the heartbeat and removing the time-motion effect. A non-real time configuration could be used almost as effectively, as represented in FIG. 8b. Here the data is processed and transferred periodically as needed. The data is captured and processed by the main processor and the result sent to a pulser computer that would pulse the excitation at the proper times.

A variation of this method but yielding basically the same result would apply a pulse to the sensor every increment of a motor encoder and determine the position of each vector in the pipeline processing.

Manufacturing of the Elongate Member

A sheath 80, as described above, may be made by first bonding a tubular portion into the catheter manifold 85 using an epoxy or other suitable adhesive. The sheath 80 should extend to a distal side of the entrance of the flush ports into the manifold 85. Care should be taken to ensure that adhesive does not flow into the lumen 86 of the sheath. Then the strain relief coil 91 may be installed into the manifold hub. The hub is then filled with adhesive. This assembly is then allowed to cure.

Using an adhesive applicator syringe with a 0.025 inch maximum diameter tip, the adhesive lumen seal 87 is installed in the distal end of the sheath 80. The seal 87 is preferably located 0.5 inch from distal tip of sheath 80. The seal 87 should be 0.100 inch in total length. Next, the distal marker coil is installed. Using a syringe, adhesive is applied to 0.05 inch of the distal end of the marker prior to installation. The distal marker is installed in the distal end of sheath 80. The marker coil is allowed interfere with the sheath's seal 87 by 0.05 inch. Then the assembly is allowed to cure at 140° F. for 4 hours.

Flushing Methods

The sheath 80 includes a means for flushing the sensor assembly 24 and sheath lumen 86. Any presence of entrapped gas or contaminants in around the sensor assembly 24 reduces the performance of the imaging system. Any gas or contaminants on the surface of the transducer sensor 42 may generate severe reflections and essentially blind the transducer in that region. The flushing process assures that all gas and contaminants are removed.

Flushing of the sensor assembly 24 and the sheath 80 may be provided by three alternative systems:

Referring to FIG. 9, a first embodiment of the flushing system utilizes a flushing lumen 93 which may be a flexible tubular member having a diameter less than the diameter of the lumen 86 of the sheath 80. The flushing lumen 93 may be fed through the catheter manifold's second port 90 proximal to the distal seal 87 of the lumen 86. The flushing lumen 93 is then pressurized with a flushing medium. The flushing lumen 93 is slowly withdrawn from the sheath 80 while pressure is maintained on the flushing medium. The process is continued until the flushing medium flows from the proximal end of the manifold's main port 89 and the flushing lumen is removed.

Figure 10:
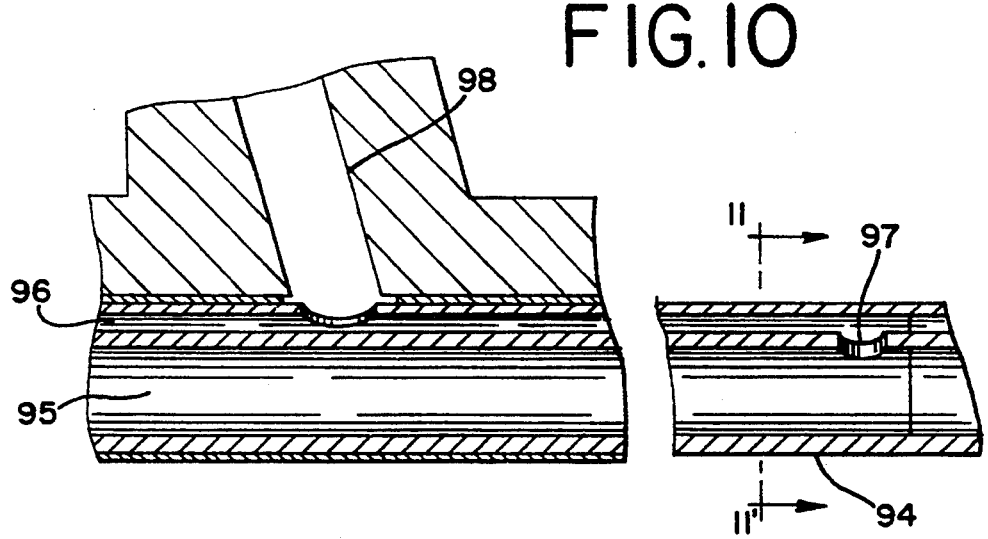
FIG. 10 is a sectional view of a second alternative embodiment of the elongate member illustrating a second flushing method.
Figure 11:
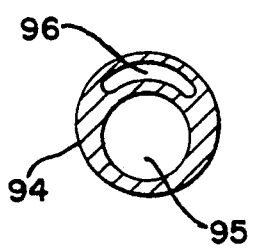
FIG. 11 is a sectional view along lines 10–10' of the embodiment in FIG. 9.

Referring to FIG. 10 and 11, a second embodiment of the flushing system is depicted. The second flushing embodiment uses a sheath 94 having dual lumens, a main lumen 95 and an outer lumen 96. The outer lumen 96 provides a flushing channel to the distal end of the sheath 94 where it communicates with the distal end of the main lumen 94 through a opening 97 between the lumens 95 and 96. A flushing medium, typically water, is continuously fed under pressure through a proximal catheter manifold's flush port 98 through the flushing lumen 96 from the proximal end to the distal end, through the opening 97 into the main lumen 95, and back through the main lumen 95 from the distal end to the proximal end until the medium flows from the manifold's main port.

Figure 12:
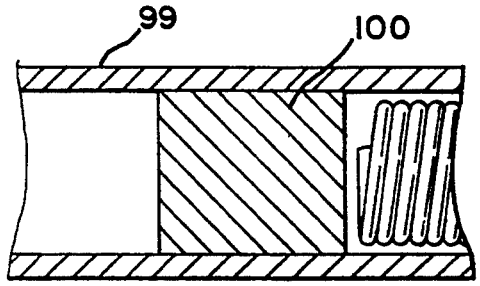
FIG. 12 is a sectional view of a portion of a third alternative embodiment of the elongate member illustrating a third flushing method.

Referring to FIG. 12, a third embodiment of the flushing system is depicted. This embodiment includes a sheath 99 having an air permeable seal 100 in the sheath's distal tip to allow entrapped gases to diffuse out during flushing pressurization. The seal 100 has a permeability which allows the air mass in the sheath lumen to be dissipated through the distal tip area in a reasonably short amount of time. In a complimentary fashion, the seal's porosity is low enough to restrict water mass transfer, i.e. the surface tension of the water coupled to the porosity of the seal prohibits mass transfer. The seal may be made with materials with permeabilities in the range of: 2 to 2,000,000 ng/(s-m-Pa). This permeability range covers both flushing pressure variations of 6.895 kPa to 689.5 kPa and flushing times of 1 second to 1200 seconds. In the preferred embodiment, permeability for sheath flushing in 20 seconds at a 202.7 kPa flushing pressure through a 2.54 mm long seal is 1290.1 ng/(s-mPa).

IV. Coupling and Uncoupling

Referring to FIG. 13, the elongate member 26 (with the distal drive cable inside thereof) is connected at its proximal end to the coupling member 30 by means of the manifold 85. The coupling (and uncoupling) member 30 connects the distal drive cable 28 to the proximal drive cable 32 which in turn connects to the proximally located components, i.e. the signal processing unit 34 and the motor 36. By means of the coupling member 30, the imaging system 20 provides a means of coupling and uncoupling the distal transducer side of the system from the proximal components at a point outside the body of the patient.

This coupling member 30 provides several advantages for the imaging system 20. Providing for coupling and uncoupling of the distal sensor facilitates loading and handling of the drive cable 28 and the sensor assembly 24 into the elongate member 26. Also, by providing a means for coupling and uncoupling, the imaging system 20 can utilize larger size, less expensive components for electrical and mechanical transmission proximally from the coupling location where the dimensions of the components are not limited by the constraints of positioning in the coronary vasculature. Thus, critical electrical information can be transferred from the rotating drive cable 28 to a less expensive, commercially available, stationary, 50 ohm coaxial cable while maintaining a mechanical link between the motor 36 and the sensor assembly 24. As required for the rest of components used for electrical transmission, transfer of electrical information by the coupling member 30 is preferably maintained in a controlled impedance environment matched to the transducer.

At the coupling location, the transmission of mechanical torque can also be transferred proximally to larger, commercially available components that are less expensive to manufacture. Further, at the point of coupling between the proximal drive cable 32 and the distal drive cable 28, a mechanical 'fuse' may be provided to prevent torsional overload to the drive cable in the body.

In the coupling member 30, the electrical and mechanical functions which are united in the same components in the distal drive cable 28, are split into separate, adjacent cables one for the mechanical transmission and another for the electrical transmission inside the proximal drive cable 32. Thus, in the uncoupling member 30, the electrical signal transmission, which in the distal drive cable 28 is conducted by the core wire that is rotating at operating speed, is transferred to a non-rotating coaxial cable connected to the proximal signal processing unit 34.

The coupling member 30 may be located approximately 60 inches proximal of the sensor assembly 24 so that it is outside of the patient's body. The coupling member 30 is comprised of a sleeve 101 inside of which is contained a matable coaxial connector pair. The coupling member 30 in this embodiment of the imaging system is provided by two assemblies that are mechanically coupled together: a transducer pin assembly 102 that connects to the components on the distal side of the system, such as the sensor assembly 24 and the elongate member 26, and a slip ring assembly 104 that connects to the components on the proximal end of the system, such as the signal processing unit 34 and the motor 36.

The coupling member sleeve 101 is formed by a first or distal sleeve portion 106 that is part of the transducer pin assembly 102 and a second or proximal sleeve portion 108 that is part of the slip ring assembly 104. These sleeve portions 106 and 108 may be made of a metal, such as aluminum. The sleeve portions 106 and 108 are held together through the use of a coupling nut 110. Accordingly, the coupling nut 110 provides the means for securing the distally located transducer pin assembly 102 to the proximally located slip ring assembly 104 and their respective coaxial connector halves located there-within together, as described below, during system operation. This nut 110 may be removed or tightened to disconnect or connect the distal components from the proximally located components.

Referring to FIGS. 14 and 15, the coupling nut 110 slidably fits over the sleeve portion 106 and abuts against a shoulder 112 on the proximal end of the sleeve portion 106. The coupling nut 110 has threads 114 internal thereto oriented in a proximal direction to engage corresponding external threads 115 on the exterior of the slip ring sleeve portion 108, as shown in FIG. 15.

In each of the sleeve portions 106 and 108, there is provided one half of the matable coaxial connector pair. As shown in FIGS. 14 and 15, a male component 116 of the matable coaxial connector pair is located in the transducer pin assembly 102 and a female component 117 of the matable coaxial connector pair is located in the slip ring assembly 104. This coaxial connector mated pair 116 and 117 provides for both the electrical and mechanical separation point between the transducer pin assembly 102 and slip ring assembly 104. Mechanical coupling between the mated connector halves is controlled by the spring force exerted by interference between the male coaxial connector shield spring contacts 118 and the female coaxial connector shell 119. This spring force generated between the male and female components of the matable coaxial pain allows for torque to be transmitted across the coupling member 30. This matable coaxial pair may be a commercially available coaxial connector pair, such as made by Amphenol Corp., modified to be connected in the coupling member 30.

This internal coaxial connection is made with a controlled impedance matched to the drive cable 28 and the transducer sensor 42, i.e. with an impedance of 50 ohms. Matching the impedance in the coupling member 30 with these components avoids mismatch signal reflections, as described above.

Referring to FIG. 14, the transducer pin assembly 102 is connected to the proximal end of the drive cable 28 so as to allow rotation of the drive cable 28 inside the transducer pin assembly 102. Located at and covering the distal end of the sleeve portion 106 of the transducer pin assembly 102 is a sleeve cap 120 having a passage 121 therethrough. The sleeve cap 120 is secured to the sleeve portion 106 by stamping or a compression fit or other means. The sleeve cap 120 includes a nipple portion 122 which extends distally and in which is located the distal portion of the passage 121. The nipple portion 122 is connected to or may be formed of the sleeve cap 120. Threads 128 located on the exterior of the nipple 122 engage internal threads located in the proximal end of the manifold 85. A compression O-ring 129 may be provided between the distal end of the nipple 122 and the manifold 85 to ensure a secure fit.

Located inside and connected to the sleeve 106 proximally from the end cap 120 is a coaxial connector bearing 130 and a bearing retaining ring 131. The bearing 130 and end cap 120 define an interior portion 132 of the transducer pin assembly 102. The bearing 130 may be made of bronze and oil-impregnated to provide for free rotation inside the pin assembly's outer shell. A drive cable clamp 134 is secured to the drive cable 28 so as to be located in the interior portion 132 of the transducer pin assembly 102. The clamp 134 may be secured to the drive cable 28 by an adhesive or other means. A strain relief sleeve 136 may be connected to or formed on the distal surface of the clamp 134 and extend distally on the drive cable 28 to a location through the nipple 122 (e.g. 0.75 inches). The strain relief sleeve 136 may be made of teflon.

Located around the clamp 134 is a shell 138. The shell 138 is comprised of a first shell half 139 and a second shell half 140 that can be secured together such as by means of threads. When the shell halves 139 and 140 are secured together, they also secure by compression the clamp 134 between them. The shell 138 include a distal opening 141 and a proximal opening 142, both aligned with the passage 121 so as to receive the drive cable 28. The opening 141 may also receive a portion of the strain relief sleeve 136. A bushing 143 may be located in the proximal opening 142. The bushing 143 may be made of teflon. Connected to the distal side of the shell 138 is the male portion 116 of the coaxial connector pair.

The drive cable 28 is thus rotatably secured within the transducer pin assembly 102. The drive cable 28, the clamp 134, the strain relief sleeve 136, the shell halves 139 and 140, the bushing 143 and the male coaxial connector 116 are rotatable.

Referring to FIG. 15, there is depicted the slip ring assembly 104 which forms the proximal half of the coupling member 30. In the slip ring assembly 104, the electrical signal is transferred from rotatable distal components to non-rotatable proximal components, i.e. the electrical signal transmission which is carried by rotating components distally is transferred to non-rotating components proximally. In addition, in the slip ring assembly 104, the electrical signal, which is carried by the same components that transmit the mechanical torque distally, is carried proximally by components separate from those that transmit the mechanical torque.

As described above, the slip ring assembly 104 includes the sleeve portion 108 the proximal end of which connects by means of the threads 115 and the coupling nut 110 to the transducer pin sleeve portion 106 to form the non-rotating coupling member sleeve 101. A slip ring end cap 158 connects to and covers the proximal end of the slip ring sleeve 108. The slip ring end cap 158 includes a first opening 160 aligned centrally therein and a second opening 162 offset from the first opening 160. Located in and extending through the first opening 160 is a slip ring drive shaft 164. A proximal bushing 166 is positioned in the first opening 160 around the slip ring drive shaft 164. An outer slip ring 167 and an inner slip ring 168 are connected to the distal end of the slip ring drive shaft 164. The outer and inner slip rings 167 and 168 are connected distally to a modified coaxial connector 170 which forms the proximal portion of female portion 117 of the mated connector pair. A proximal bushing 171 is mounted in the proximal end of the sleeve portion 108 around the female portion 117 of the mated coaxial pair.

Through the second opening 162 in the slip ring end cap 158 extend leads 172 and 174 from the proximal drive cable 32. Specifically, the lead 172 connects to the signal conductor and the lead 174 connects to the reference plane conductor of a coaxial cable in the proximal drive cable 32, as explained below. The distal end of the lead 172 connects to an inner brush ring 176 and the distal end of the lead 174 connects to an outer brush ring 178. The inner and outer brush rings 176 and 178 may be made of brass and may be approximately 0.063 inch wide. An inner spring 180 is located between the inner brush ring 176 and the end cap 158 and an outer spring 182 is located between the outer brush ring 178 and the end cap 158. The inner and outer springs 180 and 182 bias the inner and outer brush rings 176 and 178, respectively, in a distal direction away from the end cap 158.

The inner brush ring 176 bears against a set of inner brushes 184 and the outer brush ring 178 bears against a set of outer brushes 186. These two sets of brushes 184 and 186 are mounted coaxially to each other. In a preferred embodiment, each set of brushes 184 and 186 includes three brushes, (only two brushes of each set are shown in FIG. 15). Each brush is located at 120 degree intervals to the other two brushes in its respective set.

The inner set of brushes 184 and the outer set of brushes 186 are slidably held by a brush guide 188. The brush guide 188 is mounted into the inside of the slip ring sleeve 108. The brush guide 188 is a cylindrical plug having two sets of three slots each located at 120 degrees from each other (i.e. for a total of six slots) therethrough for retaining the two sets 184 and 186 of three brushes each. The brush guide 188 also includes a large central opening 189 through which passes the slip ring drive shaft 164.

Biased by the inner spring 180, the set of inner brushes 184 bears against and rides on the inner ring 168. The inner ring 168 is used to conduct the signal and is attached to the internal conductor of the coaxial connector 117. Biased by the outer spring 182, the set of outer brushes 186 bears against and rides on the outer ring 167. The outer ring 167 is used for connection to the reference plane signal and is attached to the reference plane conductor in the coaxial connector 117 and/or the sleeve 108.

The brushes provide the path for transferring the electrical signal information between the stationary inner and outer brush rings 176 and 178 and the rotating inner and outer slip rings 168 and 167. In a preferred embodiment, the brushes are made of silver graphite. Silver graphite provides for a brush material that is highly conductive and self-lubricating.

Relatively large brass slip rings are utilized to increase the conductive contact area available between both the slip rings and coaxial connector 117, and the slip ring and brushes. The use of large contact areas reduces electrical resistance and signal loss through the slip ring assembly 104.

In the slip ring assembly 104, only the coaxial connector 117, the slip ring drive shaft 164, and the slip rings 167 and 168 rotate during operation. The sets of brushes 184 and 186, brush rings 176 and 178, brush guide 188 and sleeve 108 all remain stationary during operation.

Mechanical coupling

In addition to providing for electrical transmission, the slip ring assembly 104 also furnishes the mechanical torque transmission across the coupling member 30. The springs 180 and 182 in the slip ring assembly 104 develop the friction force which supports the torsional load created by the transducer drive cable 28. Mechanical coupling between the mated connector halves 104 and 106 is provided by the spring force generated by the interference between the male coaxial connector shield contacts 116 and the female coaxial connector shell 117. This spring force creates a friction fit between the mated connector pair 116 and 117 and allows torque to be transmitted across the coupling member 30. In the preferred embodiment, the torque transmittance in the slip ring assembly 104 is tuned by adjusting the spring force to provide a maximum torque of 3 inch-ounces before relative slippage between connector halves 116 and 117 occurs. This provides for a mechanical 'fuse' feature in the system that ensures torque transmittance to the drive shaft assembly and not the pin assembly shell.

The coupling member 30, comprised of the transducer pin assembly 102 and the slip ring assembly 104, is easy to use and eliminates or reduces obstructions in the area of the patient. This facilitates the placement and manipulation of the elongate member 26 and sensor assembly 24 in the coronary vasculature of the patient without the burden of having bulky components in close proximity to the patient. The assembled coupling member 30 has a cylindrical shape of approximately 0.75 inch in diameter and approximately 4 inches in length. (The transducer pin assembly 102 is approximately 0.75 inch in diameter and 1.75 inch in length.)

The fact that the slip ring assembly 104 uses controlled impedance components for electrical transmission except for a portion of a length less than 0.5 inches. This feature provides for the reduction of signal reflections from impedance mismatches.

V. The Proximal Drive Cable

The distal end of the proximal drive cable 32 connects to the proximal end of the slip ring sleeve portion 108, as shown in FIG. 15. The distal end of the proximal drive cable 32 includes a proximal cable sheath 190 that connects to the slip ring assembly sleeve portion 108. The proximal cable sheath 190 may be formed of a section of heat shrink tubing. Provided in the interior of the cable sheath 190 are the drive shaft 192 that connects proximally to the motor 36 and the proximal coaxial cable 194 that connects proximally to the signal processing unit 34. The drive shaft 192 and the proximal coaxial cable 194 are adjacent to each other with the drive shaft 192 aligned approximately along a central axis of the sheath 190 and the coaxial cable 194 offset therefrom. Proximally from the cable sheath 190, the drive shaft 192 and the proximal coaxial cable 194 are enclosed in a proximal cable covering 195.

The drive shaft 192 connects to the slip ring drive shaft 164 inside the sheath 190. This connection is made by means of a shaft coupler 196 which may be a tubular member made of DELRIN ®. As described above, the slip ring drive shaft 164 extends distally from its connection to the drive shaft 192 into the slip ring assembly 104 through the opening 160 in the slip ring assembly end cap 158. The drive shaft 192 is preferably longitudinally flexible yet torsionally rigid so that it can rotate through operation of the motor and transmit this rotation to the slip ring assembly on to the drive cable and transducer assembly 24. The drive shaft 192 may be a flexible cable made of high tensile strength steel or stainless steel. A commercially available flexible drive shaft may be used, such as S.S. White Industrial Products, Inc. shaft #098-9.

Also inside the proximal cable sheath 190 is the distal end of the proximal coaxial cable 194. The distal end of the reference plane conductor 198 of the proximal coaxial cable 194 connects to the proximal end of the reference plane lead 174 and the distal end of the signal conductor 200 of the proximal coaxial cable 194 connects to the proximal end of the signal lead 172. The coaxial cable 194 is preferably flexible and is stationary, i.e. it does not rotate with the drive shaft 192. A matching capacitor 202 may be connected between the signal and reference plane conductors 200 and 198 of the coaxial cable 194 for impedance matching purposes. (The matching capacitor 202 would normally have a heat shrunk cover, which is not shown in FIG. 15). The proximal coaxial cable 194 may be a commercially available 50 ohm coaxial cable, such as RG 178 B/N, available from Belden Corporation.

Referring to FIG. 16, in the proximal cable 32, the drive shaft 192 and the proximal coaxial cable 194 extend proximally from the proximal cable sheath 190 adjacent to each other inside the proximal cable cover 195. The proximal coaxial cable 194 may be enclosed in an isolation shield 206 that may be made of tin plated copper braid. The drive shaft 192 in enclosed in a non-rotating metallic sleeve 208. At a branching member 210, the coaxial cable 194 and the drive shaft 192 separate. The branching member 210 may be made of a heat shrink tubing. From the branching member 210, the coaxial cable 194 extends proximally inside a coaxial cable jacket 212 to coaxial connector 214 that can be fitted to the signal processing unit 34. From the branching member 210, the drive shaft 192 extends proximally inside a drive shaft jacket 216 to a coupling connector 218 to provide for connection to the motor 36. The motor may be a 40 watt DC rare earth motor, such as manufactured by Maxon Motor Co., Model No. RE035-071-39EAB200A.

V. The Pulser and Signal Processing Operation

The signal processing unit 34 includes a pulser which generates the high energy pulses that are converted by the sensor into an acoustical wave that is used for imaging. A full single cycle pulser is used since it gives twice the energy as a half cycle pulser for the same peak voltage and further it gives better settling. For isolation between the high voltage circuitry and the elongate member, a transformer is used. High frequency transformers are easier to design for cyclic waveforms with no DC frequency component, if fast settling is important. A full single cycle pulse of the sensor generates a return signal with almost no increase in ringdown time as compared to an impulse. Any increase in the number of cycles beyond one increases the ringdown time almost directly proportionally.

For a good image, signal quality is very important. This means high amplitude with ringdown quickly to a −40 dB level. A pulser technique is utilized that provides for a sharper pulse and better ringdown of the signal. Prior pulsers implement a pulse shape of an integer number of half cycles at a given frequency. A pulser that is capable of generating a pseudo-random pulse would be able to excite the transducer and settle the reflections out by the sequence of pulses at certain amplitudes and at the right time.

Figure 17:
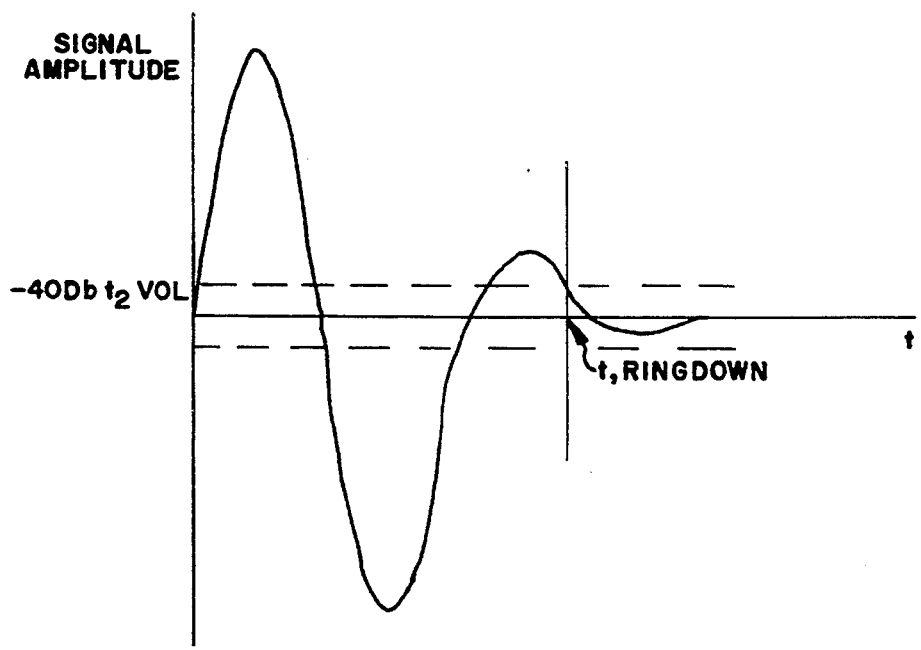
FIG. 17 is a diagram of signal amplitude versus time for the pulser in a first embodiment of the present invention.
Figure 18:
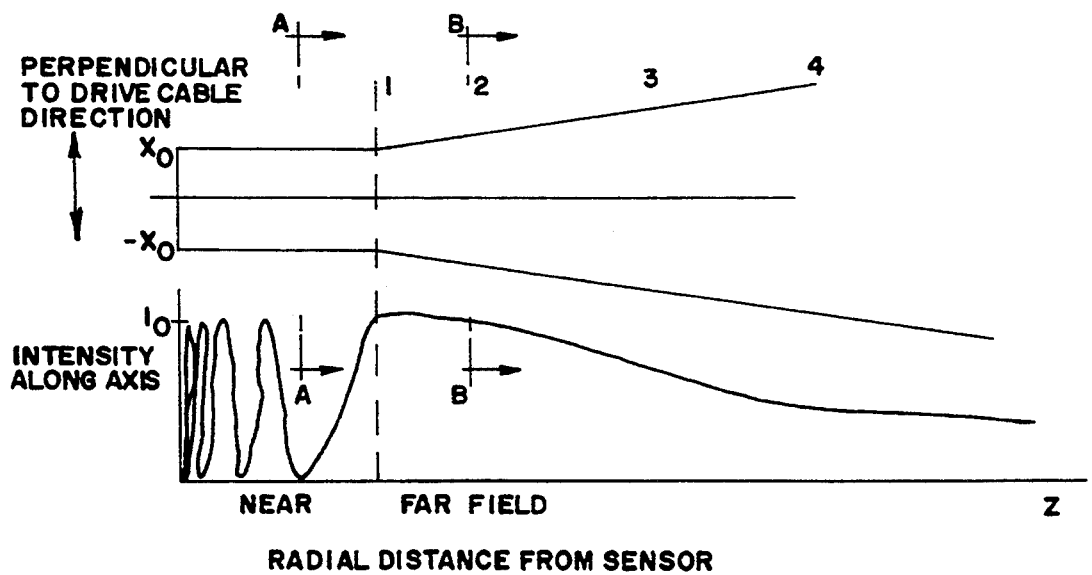
FIG. 18 is a diagram of signal intensity versus radial distance from the sensor perpendicular to drive direction.
Figure 19:
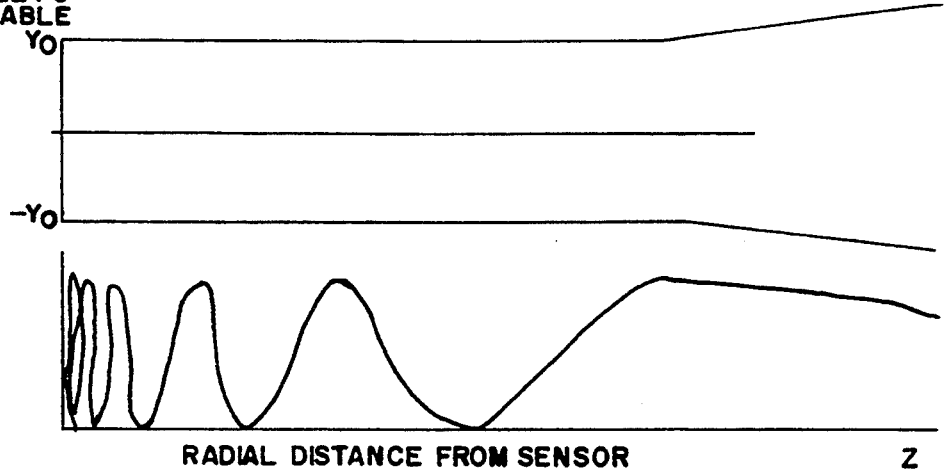
FIG. 19 is a diagram of signal intensity versus radial distance from the sensor perpendicular to drive direction.
Figure 20:
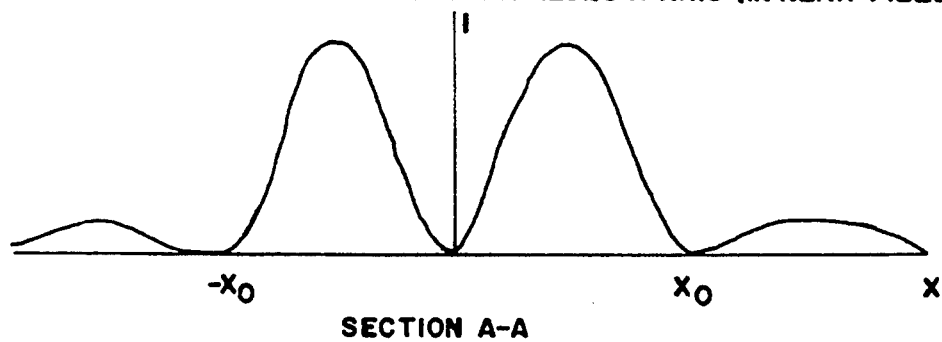
FIG. 20 is a diagram of signal intensity versus the position along the cross section A–A' of FIG. 18.

As mentioned above, the size and shape of the sensor window is directly related to the quality of the ultrasonic image obtained. Ultrasonic imaging in two dimensions, (i.e. of a cross section of the arterial wall) is acoustically a three-dimensional problem. Referring again to FIGS. 2-4, the objective for a good imaging system is to have a thin sharp rotating beam over the distance of interest, e.g., in a direction, y, radial to the artery wall. However, the beam, of course, propagates in all directions. The performance of the beam in the two lateral directions from the radial direction is termed the acoustical optics of the sensor. In the two lateral directions $x_1$ and $x_2$ (i.e. the directions perpendicular to the radial direction), the beam shape is a function of the distance from the sensor, sensor focus, physical shape and the operating frequency. For an imaging device that makes circular scans of the arterial walls, the resolution in the radial direction is limited by the number of cycles of propagation of the pulse waveform. This time or distance is determined typically by the −40 dB amplitude points of the waveform, as illustrated in FIG. 17.

Using a rectangular transducer sensor is one of the keys to making a very small intravascular ultrasound device for use deep in the coronaries. There are some tradeoffs with respect to circular apertures, but at the very small sizes the best performance is obtained from a rectangular aperture.

The beam shape is a function of the housing aperture size in the respective direction. This function is $$Z = A^2/L$$

where Z is the near field distance, A is the aperture size, and L is the wavelength. For the above 0.5×1.0 mm window with a 0.056 mm wavelength (as defined by the frequency and media speed of sound), the near field is 1.1 mm in the x directions and 4.5 mm in the y direction. The significance of the near field is that, for an unfocused sensor, the beam width is nearly the aperture width through the length of the near field. In the near field the beam is rapidly changing in all directions. This is from the constructive and destructive interference patterns. In the far field the beam is more uniform and diverges. The far field behaves as though the source was a point source. For focused crystals the beam can be focused up to the limit of the near field. A focused beam is narrower in the focused region but diverges faster than unfocused outside this region.

For intravascular ultrasound in the coronary region, it is sought to obtain images out to about 5 mm in radius. For a window having dimensions such as described, an advantage of the rectangular shape is that even though the energy is spreading in the x directions, the energy in the y direction remains relatively constant through the distance of the region of interest, as illustrated in FIGS. 18-21. In the x directions, or lateral directions as used in this specification, the beam size is quite usable to generate good intravascular images throughout the radius of interest. For a circular aperture of this size, the intensity would decrease very rapidly since the beam is spreading uniformly in all directions. The rectangular aperture has better distance vs. energy dropoff along with a larger surface area. For apertures 0.5 mm and smaller the rectangular shape has some characteristics that are more desirable for apertures than circular shapes.

Calibrated Waveform Pulser

As mentioned above, for radial resolution the ringdown of the signal is very important and it would be desirable to have a single cycle response to a impulse excitation. Typically, the excitation that is used is either a half cycle type impulse excitation or a integer number of sine wave cycles.

There are significant advantages to using an excitation that uses a main pulse rather than a modified pulse waveform to cause a faster −40 Db ringdown time. There are two major reasons for this. From computer modeling of the transducer, the resultant objective of the iterative optimization program is to generate a system transfer function that has a smooth phase and magnitude over the widest frequency range. This is achieved by optimizing the value of peak pulse amplitude squared divided by the integral of time weighted magnitude after the peak. By using a non-impulse excitation, the Fourier transform of the excitation is different so that the frequency spectrum of the excitation is different than an impulse. The ideal impulse has constant magnitude frequency components. By allowing the computer to vary the waveform from one discrete time increment to the next, an optimum excitation waveform can be generated.

There are limitations of the computer model, such as non-infinite backing distance, surface irregularities, mechanical tolerances, impedance mismatches, etc. These variables result in the performance of the actual device to depart from what the model predicts. By using basically the same technique to calibrate a device, certain reflections and imperfections can be countered by using an optimized excitation.

Figure 22:
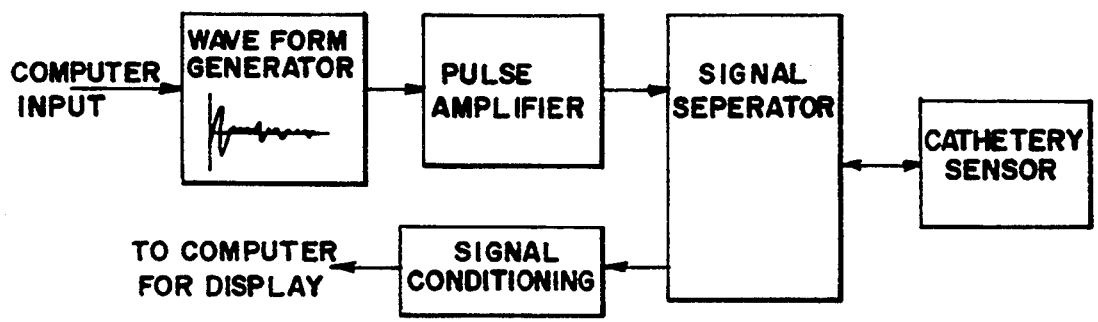
FIG. 22 is a block diagram of the calibrated waveform of the pulser.

This circuit could be implemented using a high speed Digital to Analog (D/A) converter, where the output could be programmed by a computer to a predetermined wave form, (see FIG. 22). This output could be amplified to any required level that is required. The optimized waveform is generated over a few hundred nanoseconds and is settled out before the image data is received.

VI. Additional Preferred Embodiments

A. Sensor Constructions

Figure 23:
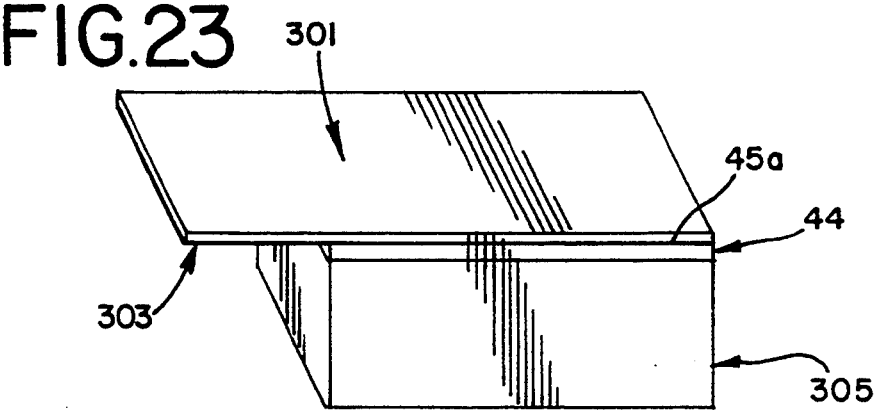
FIG. 23 is a perspective view of another embodiment of the transducer sensor.

Referring to FIG. 23, there is depicted an alternative embodiment for the construction of the transducer sensor. In constructing a sensor, it is desirable to have a configuration that gives a uniform beam from one device to the next and is easy to produce. A uniform beam is necessary for both good repeatability of system performance as well as for implementing other, more advanced data conditioning algorithms necessary for image enhancement.

Referring to FIG. 23, there is depicted an alternative embodiment of the transducer sensor. As in the embodiment described above and illustrated in FIGS. 2-4, the transducer sensor in FIG. 23 is comprised of a several separate layers including a transducer core, conductive layers bonded to either side thereof, a backing layer and a matching layer. In the embodiment shown in FIG. 23, a matching layer 301 (which may be composed of a PVDF material) is larger in dimension than sensor core 44 and includes a overhang 303 on a proximal end. This overhang 303 allows electrical contact between the conductive surface 45a over the sensor core 44 and the center conductor of the coaxial drive cable (not shown). This provides for both a superior transducer surface with a very uniform active area. This embodiment also significantly facilitates manufacturing. These features can be further enhanced through the use of a conductive backing 305. The conductive backing 305 provides an electrical contact between the sensor back surface and the sensor holder. The sensor holder is electrically connected to the drive cable outer conductor (not shown). The conductive backing can be composed of a number of different materials, such as silver, tungsten, copper, gold or a number of other elements or alloys. The matching layer 301 can be made from PVDF, or other materials.

Other alternative embodiments include using a PVDF type material having a conductive layer on both the front and back face of the sensor to carry the signals to their connection. Behind the layer on the back side of the sensor an attenuating layer may be needed to absorb the energy coming off in that direction. The two connections would be terminated at the drive cable coaxial electrical connections. A further alternative is to extend the conductive faced matching layer and the conductive faced backing layer from the sensor core to the proximal portion of the drive cable by integrating the flexible circuits into the construction of the drive cable. In order to electrically insulate the two conductive surfaces, an insulation layer is incorporated between the layers. This would require no joints in the electrical sensor construction within the catheter.

B. Imaging Guide Wire

An alternative embodiment of the present invention may combine the functions of a guide wire with those of an ultrasonic imager. A guide wire function is to navigate to a location of interest in a patient's vasculature and to position a catheter over the guide wire into place for a procedure, such as balloon angioplasty. Because it would be desirable to have a device that would image the artery before, during and after such procedures, it would be advantageous to combine the functions of the guide wire and the imaging device. Most catheters are of a coaxial design so that once the catheter is in place the guide wire could be withdrawn and an imaging guide wire put in its place.

Currently guide wires are used in dimensions of 0.018 inch or smaller. In the embodiment described above, the drive cable 28 has a diameter of 0.026 inches and accommodates a transducer sensor having an active area of approximately 0.020×0.040 inch. In order to combine the functions of the drive cable with those of a guide wire, the dimensions of the drive cable would be reduced in size to approximately 0.018 inch in diameter. The transducer sensor would be made with a housing aperture close to 0.017 inch. At that size the image resolution would be substantially the same as in the embodiment described above. With image enhancement techniques described elsewhere in this specification, it would be possible to have an image as good as or better than those currently achieved. A thinner transducer having a higher frequency or a different material could be used for the sensor.

Figure 24:
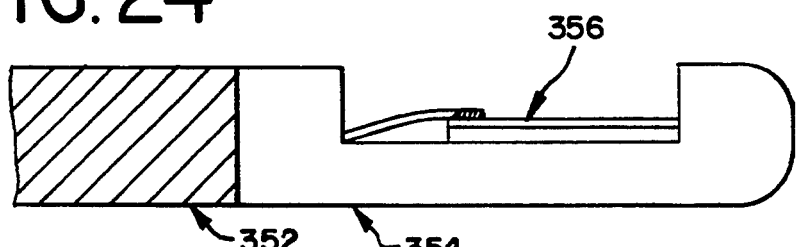
FIG. 24 is a plan view of the distal end of an imaging guide wire which is another embodiment of the present invention.

A distal end of an imaging guide wire 350 is illustrated in FIG. 24. A drive cable 352 can be constructed substantially as described above, except that for reducing the size from 0.026 inch to 0.018 inch, two coils and a double braid would be used instead of three coils and an eight wire braid. This has the result of reducing the outer coils and conductors to 0.008 inch leaving 0.010 inch for a center conductor and insulation.

In one aspect, the construction of the imaging guide wire would likely depart from that of the embodiment described above and that is in the mounting of the transducer sensor to the drive cable. In the imaging guide wire, the width of the active area of the sensor would be nearly equal to the diameter of the drive cable. In all other respects, the construction of the transducer sensor portion of the imaging guide wire would be very similar to that of the embodiment described above. This drive cable 352 has a sensor holder 354 mounted at the distal end thereof. Unlike the sensor housing described above having oppositely located windows, the sensor mount 354 of this embodiment would not include a second window located oppositely from the transducer opening. Instead, the mount 354 would provide physical support under the transducer sensor 356. Also, due to size constraints, there would be little room for backing material on the back side of the transducer sensor. This could be compensated for by several different methods. For example, the sensor could be made from a copolymer material which has a low acoustic impedance so that no matching layer would be needed to couple to the fluid and further the impedance difference between the backing support and the sensor material would be large enough so much less energy would enter into the backing compared to PZT directly mounted. Alternatively, the energy that enters into the back support can be somewhat dissipated and scattered by using a material such as a porous sintered type metal for the backing support and canceling out reflections with a calibrated pulse waveform. A major problem with copolymer materials is the lower D33 coefficient. (D33 is the dielectric constant in the thickness direction.) This makes a sensor of the same surface area have a larger impedance. This impedance difference could be compensated for by using some of the techniques described elsewhere within this specification or active circuitry could be placed next to the sensor to buffer the signal to a lower impedance.

PZT materials can also be used in the imaging guide wire embodiment, but they would likely need a front matching layer and a back decoupling layer. The backing configuration may include a half wave decoupler where its impedance is low with respect to both the sensor and backing support. This backing decoupler would work in the opposite manner from that of the matching layer, i.e. where a quarter wave length aids in coupling, a half wave length thickness helps in decoupling energy transfer between two impedances.

In the imaging guide wire, the electrical connections would be made through the backing support to the back side of the sensor and to the outer conductors of the drive cable. The front connection would be made the same way as in the embodiment described above. For the copolymer alternative, connections would be made using one of the center drive cable wires and connecting the leads directly to the metallized copolymer surface using conductive epoxy or low temperature solder.

C. CCD Data Capture and Sensor Configurations

Among the major obstacles associated with ultrasonic imaging configurations are the matching of impedances between the sensor and the signal cable, transmitting the signal down the cable with minimal loss, and maintaining a high signal to noise ratio. For phased array sensors, described below, and two dimensional sensor arrays, there are additional problems related to parallel signals, such as crosstalk and multiplexing limits.

In a further embodiment of the present invention, an imaging transducer sensor is provided having a charge coupled device, (CCD), associated therewith. The CCD is an integrated circuit that could be used to capture the high frequency waveform of the sensor and send it back to the proximal end of the device preferably both amplified and at a lower frequency. The charge coupled device (CCD), as referred to herein, may be one of a family of charge transfer devices which may also include charge injection devices.

Figure 25:
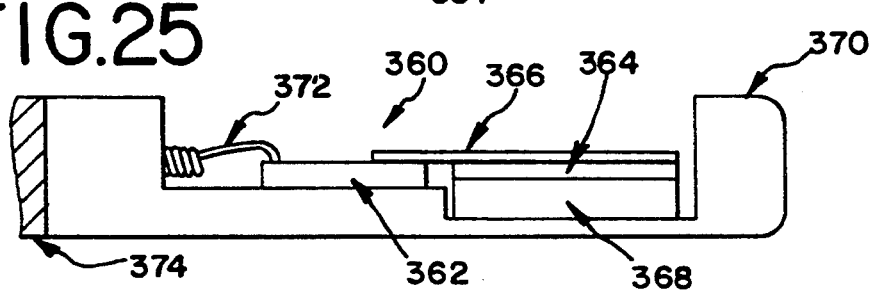
FIG. 25 is plan view of yet another embodiment of the sensor housing of the present invention.

Referring to FIG. 25, there is depicted a distal end of a imaging device 360 including a CCD 362, a PZT transducer 364, a matching layer 366, a backing material 368 all mounted in a holder 370. The signal from the transducer 368 is input to the CCD 362. The electrical connections 372 between the CCD 362 and the signal and power wires 374 would be made using standard IC wire bonding techniques. The input impedance of the cell can vary widely based on the cell capacitance and input resistance. This input impedance would be designed to give the best pulse ringdown. The pulse is generated by the CCD IC or alternatively the pulse may come from a proximal pulser, as in the embodiment described above. After the pulse, the CCD would be clocked to store the input waveform from the sensor 364. After the waveform is acquired, further clocking of the CCD array at a slower frequency will allow the "reading" of the stored value and transmitting this to the proximal electronics for further processing and display.

The device 360 provides numerous advantages for intravascular ultrasound imaging. It allows nearly perfect impedance matching independent of the sensor. It allows the reduction in frequency of the transmission of the signal to the proximal end at very low noise susceptibility or emission. This would allow the reduction of the current coaxial wire design to a single wire signal design. As few as two wires would be necessary if the pulsing is remote and communications are done over the power lines.

In the embodiment shown in FIG. 25, the CCD 362 and the sensor 364 are next to each other. By using a PZT sensor with PVDF matching layer with an overhang tab for top contact connection, the connection between the sensor and the CCD is made by having a large metal pad on the IC to contact the PVDF conductive layer.

Figure 26:
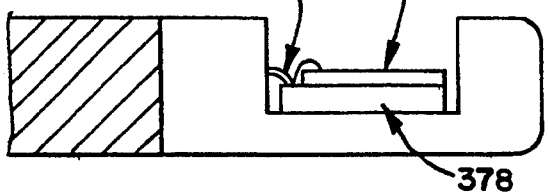
FIG. 26 is plan view of still another embodiment of the sensor housing of the present invention.

In an alternative embodiment 375 shown in FIG. 26, a transducer 376 located over a CCD 378. This embodiment uses a copolymer material for the transducer 378 and mounts it over the CCD 378. This provides an electrical sensor plane as part of the CCD 378 by using a large area top conductive layer.

In further related embodiments, a CCD array can be used in sensor devices having more than one sensing area, e.g. phased arrays and linear arrays such as described in the specification below, for sequential sensors mounted along the axis of the device for 3-D imaging. Such embodiments utilize the same type of circuit for the CCD array as described above but use parallel paths. Such a configuration is similar to that currently being used in cameras. The CCD imaging catheter functions as follows. Photons excite the electrons that are stored into a 2-D CCD shift array. Once the values are loaded into the shift array, they are then shifted to one edge of the IC one row at a time where they are shifted in the other dimension to a circuit that measures, amplifies and sends out the information one pixel at a time. A device very similar to this could be used in phase arrays, where like the single sensor CCD, the signal is read and input into the CCD at one end of the shift register and it comes out the other end. This would allow the simultaneous acquisition of all of the sensor array elements and allow the transfer of the total information to the proximal circuitry with very little loss or distortion from noise or crosstalk. Here, as in the single sensor design, the sensor material could be located over the CCD or next to it.

This concept could be extended further in an embodiment of a CCD acoustical sound beam imager. This device would be similar to that of CCD arrays used in cameras, however, instead of having a cell area designed to generate electrons from a light source, the charge could come from a small area of piezoelectric material. The piezoelectric material could be placed over the CCD surface areas would be defined on the top metallization layer of the IC that would capture and transfer the piezoelectric charge into the input cell of the 2-D shift register array. Once the data are loaded into the shift array, they are then shifted to one edge of the IC one row at a time where they are shifted in the other dimension to a circuit that measures, amplifies and sends the information out one pixel at a time. This device would be able to take a snapshot of all the acoustical 2-D wave front one point in time.

This concept could be even further extended to provide for a shift register for each of the acoustical pixels. This would allow for capturing all of the 2-D waveforms in time. Such a device would be very useful for 3-D imaging in a non-moving device. A forward-looking configuration could be constructed in which the device is placed at the end of the catheter or is placed behind an acoustical lens in the focal plane. This would allow the acquisition and direct display of the image within the focal region of the device. Acoustical excitation could be generated by a single pulse from a dispersive acoustical generator. This generator could be a piezoelectric layer over the CCD.

D. Sequential Sensor Mounting for 3-D

Three dimensional (3-D) images would be very useful to visualize the extent of certain diseases present in vessels. 3-D imaging allows for slicing, rotating and displaying the information so that volume and cross sections can be visualized. A 3-D reconstruction requires information from a number of 2-D cross sections as well as information about their corresponding position along with the vessel. Acquiring information for 3-D reconstruction can be obtained by starting at one position in the artery and moving the sensor past the area to be reconstructed. There are drawbacks associated this technique, however, such as the fact that in coronary arteries the rotational axis of the artery is hard to define in time since this axis is moving. Also, obtaining good distance measurements along the length of the artery can be difficult because of the stretching of the drive shaft or the sheath especially if the whole catheter has to be moved. This stretching can present a problem since the displacement distance may be measured proximally with a distance transducer. For example, as the catheter or the drive shaft is pushed in from a proximal end, friction could prevent the sensor from moving at all. This would produce a significant distortion in the 3-D reconstruction. Also, the duration of time needed to acquire all the information required for a 3-D reconstruction could be a drawback by limiting the capability for rapid update of the 3-D image.

Referring to FIG. 27, there is depicted a distal end of an ultrasonic imaging device 390 that provides for 3-D imaging. This device contains multiple sensors 392 along its axis. The multiple sensors 392 are located and mounted in a mounting holder 394 which is mounted on a distal end of a drive cable 396. The holder 394 would be connected to the drive cable 396, and driven thereby, in a manner similar to that used for mounting a single sensor holder. The multiple sensors 392 may include an arbitrary number of sensors depending on the number of cross sections required. Each sensor would be located at a constant, known spacing in the mounting holder 394. The sensor holder 394 may have flexible sections 398 between each of the sensors so that each of the sections can flex as it is being rotated. This could also facilitate delivery and use of this device. Each of the multiple sensors 392 would be operated to scan the cross section where it is positioned.

There are alternative transmission schemes for transmitting the information signals from each sensor section to the proximal end of the device. For example, the signals from all the sensor sections could be transmitted in parallel, or alternatively, signals from each individual sensor section could be transmitted one at a time by multiplexing, or a combination of these two methods could be used. A multiplexer would select which sensor section is currently active and send its signal down the cable. There may be some advantages in transmitting one signal at a time using a multiplexer at the proximal end of the sensor array, such as a reduction in crosstalk between channels and the elimination of multiple high frequency signal wires.

The conditioning hardware for reconstructing a 3-D image in a reasonable amount of time may include parallel processing units each working on a section of the image. Each one of these could require a powerful processor. Economies may be provided by using a network of Intel I860 type processors. The data acquisition and data pipelining would be very similar to that described elsewhere in this specification. The 3-D processing might be best implemented in the raw data pipeline. Alternatively, it could be implemented as a parallel data path into a graphics pipeline allowing simultaneous display of one of the sensor's cross section being displayed in real time along with a 3-D image of the total region.

In a further embodiment, these multiple sensors could be used in a phased sensor operation in which the beam is swept and pointed along the axis of the device. This may be a desirable configuration since it would allow some "forward-looking" along with 3-D acquisition. If this were implemented, it would be preferable that the sensor elements be constructed having a smaller dimension in the direction along the device axis.

For a sensor array configuration, the sensor sections would not have to be rotated to obtain an image. By holding the device motionless, an image would be obtained of a cross section of the wall of the artery facing the sensors. This would for most applications be very useful information. 3-D information could still be obtained by rotating the whole device.

E. Acoustical indexing for 3-D

An alternative approach to 3-D imaging is shown in FIGS. 28 and 29. This alternative approach would use a longitudinal indexing pattern 400 on a sheath 402 for 3-D imaging. The indexing pattern could be made to vary along the length of the sheath 402. The pattern 400 would be used to determine the location along the length of the sheath 402 at which the transducer (which would be insider the sheath as in the previously described embodiments) is located. This information could be used for acquiring 3-D information of the artery as the transducer was moved with respect to the sheath. The pattern 400 could be posess a binary pattern, a gray scale pattern, or other patterns to indicate a change in position between the sheath and the transducer. The pattern could be applied over Just the distal length on the sheath or over the entire length.

The pattern 400 may be encoded for incremental or absolute registration. For incremental registration, only one bit of information would be required. In such a case, external direction information would typically be generated. For absolute registration, two bits of information would be provided and used in quadrature, thereby allowing the direction to be determined. For absolute position information, gray scale encoding may be preferable. Gray scale coding has the property that only one bit changes in going from one state to the next. This prevents errors compared to binary scale for example, since there is no way of ensuring in binary scaling that all bits will change simultaneously at the boundary between two encoded values for binary or other codes.

Patterns for both radial acoustic indexing and 3-D lateral indexing may coexist on the sheath. Both patterns could be formed of the sheath material or could be formed of different materials. One pattern could be formed on the inner side of the sheath while the other on the outer side. Also, these patterns could be formed on the same surface.

F. Hydraulic Drive and Acoustic Indexing

Using acoustical rotational indexing allows determination of the sensor angular position independent of the proximal angular position of a mechanical drive shaft or cable. With this capability, means other than a mechanical drive shaft can be used to scan the vessel with a rotating acoustic beam. In a further embodiment of the present invention depicted in FIG. 30, there is provided a rotating imaging device 408 for scanning of a vessel of a patient with a rotating acoustic beam that is driven by means other than a mechanical drive cable. In the embodiment shown, a rotatable mirror 410 is driven by a rotating hydraulic source 409. The rotating hydraulic source may be a jet and fin type turbine 412. The turbine 412 would propel the mirror 410 in a rotational direction. The speed of rotation of the mirror 410 could be controlled by varying the fluid flow rate. Using fluid, the rotation of a mirror 410 would be very smooth since there would be little friction from rotating shafts compared to mechanical drive devices. Bearings 414 could be provided to provide for smooth rotation. Feedback to the pulser for pulsing and speed monitoring would be provided using an acoustical indexing pattern 416 on the sheath in the rotational direction as described above. A transducer sensor 418 could be mounted either distally or proximally from the mirror and aimed to direct an acoustic pulse toward the angled face of the rotating mirror 410.

This configuration provides advantages for combining other functions into the device. With no moving parts over most of the length of the device, there is available substantial room to add other features. For example, it would be possible to integrate a balloon onto the device. The hydraulic course would already be present, and if the balloon is ported to the same fluid used for driving the mirror, all that would need to be done to inflate the balloon would be to control the input pressure independent of the output flow rate. This could control both the inflation pressure as well as the mirror rotation speed.

In a further embodiment, a rotating sensor 420 could be used instead of a rotating mirror by using a slip ring holder 422 to couple the signals to and from the rotating sensor 420 to a signal cable on a catheter, as shown in FIG. 31. A hydraulic turbine 424 would drive this device just as described in the embodiment above with the mirror. As in the previous embodiment, an acoustic encoding pattern 426 would be included on the sheath portion of the device. This embodiment has the advantage that the sensor 420 could be designed with a thin backing with a hole therethrough large enough for admitting a guide wire 428 through the center of the device. This would provide for over-the-wire placement of the device.

G. Data Graphics Pipeline Architecture

In ultrasonic intravascular imaging, a large amount of data needs to be processed between the transducer being pulsed and the image being displayed and various means can be used for this processing. For example, processing can range from all analog to all digital. In most digital systems, the conditioned signal is acquired through data acquisition, processed by a computer, and displayed through some graphics hardware. This can be accomplished over a computer buss as long as there is a limited amount of transferring being done. Current systems are very basic in the digital conditioning and image processing, and can utilize this approach.

Figure 32:
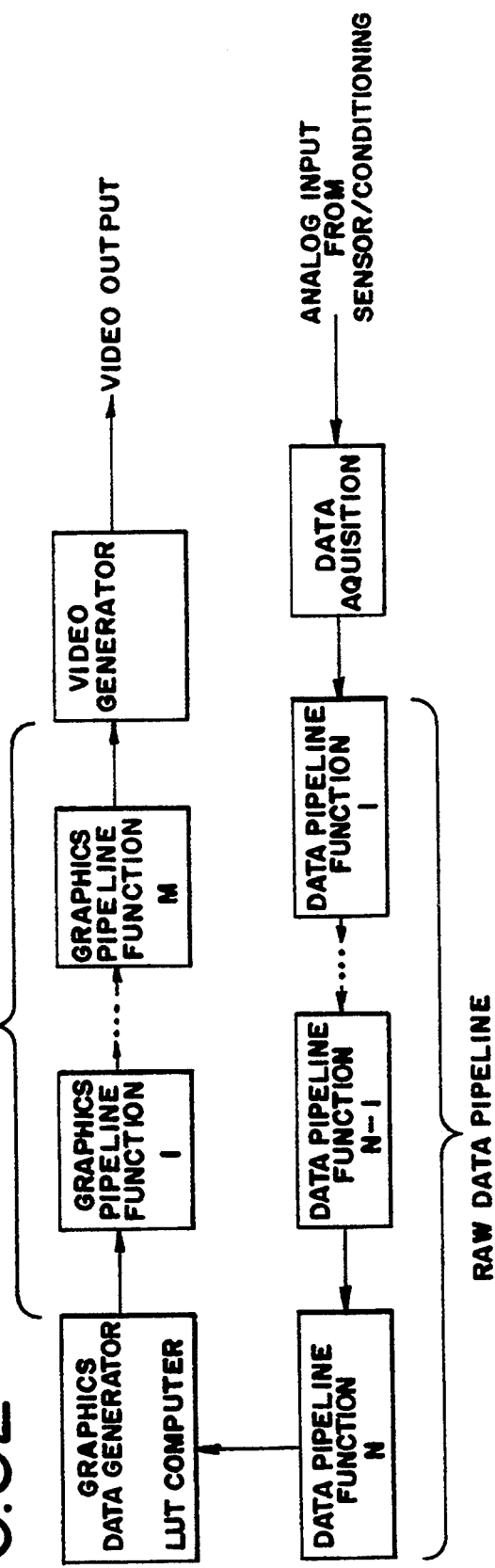
FIG. 32 is a block diagram of the data and graphics pipeline of an alternative embodiment of the present invention.

It would be preferred to use digital conditioning functions to enhance the ultrasonic image or to provide for feature extraction. This would likely require a different data flow architecture to provide for additional data transfers needed to produce the image reasonably quickly. FIG. 32 depicts a pipeline structure that provides this architecture. This architecture includes a dual pipeline: one for raw data and another for graphics data. The analog input from the sensor/conditioning is acquired from a high speed data acquisition circuit. This circuit synchronizes the raw data pipeline and transfers the data down the pipeline at a lower speed. The data is passed from one function to the next in real time or near real time speeds. This pipeline basically processes polar data. Since there would be much less data in the polar domain, it would be preferable to process this data as much as possible. These processing functions may include deconvolutions, fourier transform processing, neurocomputing processing or other techniques to enhance the raw data and do feature extraction.

At the end of the raw data pipeline, the data is converted to a graphics data stream through a large "look up table" (LUT). This LUT essentially performs a polar to rectangular conversion. There are other ways to generate the graphics data from the raw data, but this is the preferable method. The graphics data can then be handled in the graphics pipeline. Processing functions performed here are those that preferably should be done in rectangular instead of polar coordinates. These may include edge detection, area calculations/manipulations, logical pixel edge smoothing, other area operations, and image overlays.

This architecture is ideal for intravascular imaging applications since the data can be acquired and processed from one function to the next with minimal time delay. The pipeline structure is very flexible for feature enhancements and additions, all that needs to be done is to change a cable between the appropriate location to add a new pipeline function. This structure is can accommodate a variable number of pipeline elements, as needed.

A small variation on this architecture would include the addition of parallel pipelines. This could be done for example by taking the raw data acquisition output, branching off to a second LUT, and combining the two at the initial graphics pipeline function. This would allow two displays of the same raw data at the same time in different locations on the screen. This would be desirable if a real time enhanced display is desired while at the same time showing a slower 3-D reconstruction or enhanced feature detection.

H. Acoustic Waveform Deconvolution

A major goal in acoustic imaging is high resolution of the image. It is desired to have an image with features as well defined as possible. One of the limitations to the image resolution is the attenuation of the signal with frequency. If there were a much higher signal to noise ratio, a higher frequency could be used, yielding a higher resolution image for a given size aperture device. Alternatively, a smaller device could be produced having the same resolution. Resolution may be defined as the distance at which two points are barely distinguishable. With acoustic beams using traditional imaging techniques, the resolution of the image is a function of the beam width at the points of interest.

In ultrasound imaging this is complicated by the fact that coherent acoustic fields are being used, so at a certain distance apart two reflectors can appear as one or two objects depending on the interference phase. This interference pattern or "speckle" can give a sense of higher resolution object separation than is actually possible with a beam of a given width. This speckle pattern can be useful because it gives a material a texture that can be meaningful for associating certain properties or identifying the material.

In the near field, an unfocused beam varies rapidly from point to point radially from the sensor surface as well as laterally through the beam. Quantifying and defining resolution is difficult in the near field. Imaging in a more uniform beam can provide a more predictable result. In a focused beam, there are two regions where the beam is somewhat predictable. In the far field, the beam is of the form of an airy disk for a circular aperture and a mathematical $Sine^2$ function for a rectangular aperture.

For signals, convolution is the summing in time of a finite pattern input into a output pattern using a transfer function. Deconvolution is the reverse process where from a given output the input pattern is found. For deconvolution, the accuracy of the determined input is a function of the accuracy of the measured output function and the accuracy of the transfer function.

A transfer function also exists for acoustical imaging but is in two dimensional space and time as well. The two dimensional space transfer function is proportional to the intensity of the acoustical beam at a given radius. This problem is more difficult than the one above but the same basic principles apply.

For acoustic beams, a knowledge of the beam shape and point intensity as a function of time is the major variable in performing a deconvolution on the acquired information. The beam shape and point intensity values are a function of sensor aperture, surface, uniformity, sensor construction tolerances, and diffraction/reflection of where the beam has come from and gone though. To know the beam values to any great detail is a very time consuming task if they are computed or measured.

In the near field and not in a focused region, the beam shape is varying rapidly as distance from the sensor changes. In the focused region and in the far field, the beam is more uniform and predictable. In these regions deconvolution will be of some use. In the other areas of the beam as sensor technology produces more uniform sound beams, this technique will enhance the entire image. For the current system, most of the imaging is done in the far field in the rotationally lateral direction.

The resulting benefits from this routine are a sharper apparent resolution and a higher signal to noise ratio. The side lobes magnitude and the main beam size are the main determinates of the resolution of the image. Deconvolution will improve upon the limits set by both of these factors. The noise is reduced if the noise waveform has a small similarity with the acoustic transfer function, which is mostly the case.

The standard technique for performing a deconvolution is to use Fourier analysis. This is done by taking the Fourier transform of the output, dividing this by the Fourier transfer function, taking the inverse Fourier transform, and using the result. For a system where the transfer function is varying with time and space, the exact procedure is more complicated than this simple example. This is a very time consuming routine for current conditioning equipment, but a parallel network of processors could be built into the previously mentioned data pipeline in a direct or a parallel manner depending on how fast the process is and how much improvement in image results.

I. Neural Network Feature Detection

Feature detection is a very complex problem. The goal is to enable the computer to identify and label various layers of the artery and atheroma. A type of atheroma that is truly identifiable from the pattern displayed is calcific plaque. This is unmistakable to the eye as indicated by a bright area with a blocked out region behind. Even though it is easy for a human to learn how to identify this feature of the displayed image of an atherosclerotic diseased artery, it would be very difficult to write a program to identify and mark the region. Image processing and technology for object and feature detection is currently in a very early stage as far a technical sophistication. Most computer object detection is performed by performing a sequence of image transformation operations. The correct sequence is usually found iteratively by trying different combinations of the operations from a library of operations. Correct object detection is still a probabilistic event where certain combinations have a higher hit ratio than others.

Other techniques could include doing fourier analysis or other mathematical modeling techniques to analyze the data to determine the different features. From some of the published initial analysis of the materials, it is seen that most of the materials that must be distinguished from each other for feature detection have very close physical properties. The acoustical properties that are of concern are acoustical impedance, impedance variation, texture, density, velocity, attenuation all a function of frequency. Even if there is some exhibited variation in the physical parameters, it is still a formidable task to correlate the variable from the information acquired from ultrasound data.

Neural networks have been found to be very useful in solving a number of very difficult problems. They are being used currently for speech recognition, autonomous vehicle guidance and many other complicated problems like this one where there are no clear and fast rules to model the inputs to the desired outputs.

Figure 33:
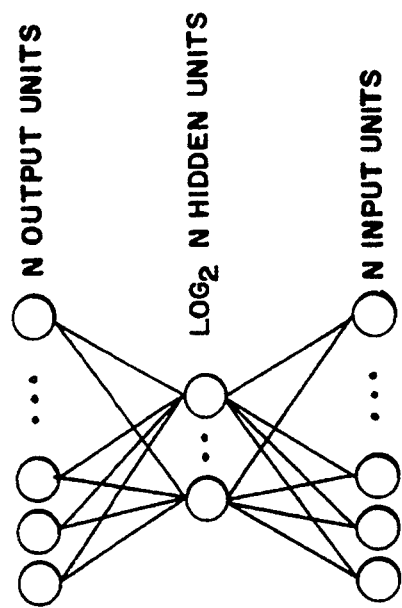
FIG. 33 is a diagram illustrating utilization of a neural network architecture in an alternative embodiment of the present invention.

Neural networks are a scalable architecture defined as a number of weighted summing nodes organized in a layered manner. In FIG. 33 there is depicted a diagram illustrating interconnections of a three layer network. Each layer node feeds its value forward as well as feedback to other layers. They can have any number of layers as well as any number of nodes per layer.

The major advantage to neural networks is that the correct weighings on the input nodes can be determined by a learning process. The network is programmed by exposing it to inputs and telling it the correct output. By doing this repeatedly with many examples the network can determine what the weighing values need to be to give the most accurate answer.

Determining the features in an ultrasound scan of an artery using neural networks is the best approach. After the network has learned the correct responses, a circuit could be developed to process the data in real time. Initially the network would be designed to operate on the data going through the raw data pipeline. Here, the network could work on a limited number of vectors at one time as inputs. This would keep the circuitry down to a practical level of parts. Handling the input raw data from one vector would require handling 500 points. For a number of complete vectors to be processed a large number of inputs result. A more reasonable approach is to use a network that processes a limited number of points from each vector and use more vectors. A circuit handling 25 radial points and 5 to 10 vectors could be developed with presently available hardware and yet contain all the neighborhood information from the acoustic beam that would be useful in reducing the data to an output feature.

It is intended that the foregoing detailed description be regarded as illustrative rather than limiting and that it is understood that the following claims including all equivalents are intended to define the scope of the invention.

We claim:

1. A drive cable for use in an imaging device for ultrasonic imaging of small vessels of a patient's body, the imaging device having an elongate member with a distal end positionable within a small vessel of the patient's body and a proximal end positionable outside the body, a transducer located at a distal end of the elongate member and operable to scan the vessel walls, the drive cable being electrically connected to a proximal end of the transducer for conducting pulses to and from the transducer, a signal processor operable to send and receive electrical signals to and from said transducer, the drive cable being electrically connected to the signal processor for conducting pulses to and from the signal processor, and the drive cable further comprising:

a rotatable outer layered coil assembly;
   a core wire located inside of said layered coil assembly and connected thereto for rotation therewith and
   wherein said outer layered coil assembly further comprises a plurality of coaxial coil layers around said core wire
   wherein said plurality of coaxial coil layers comprises three coaxial coil layers around said core wire.

2. A drive cable for use in an imaging device for ultrasonic imaging of small vessels of a patient's body, the imaging device having an elongate member with a distal end positionable within a small vessel of the patient's body and a proximal end positionable outside the body, a transducer located at a distal end of the elongate member and operable to scan the vessel walls, the drive cable being electrically connected to a proximal end of the transducer for conducting pulses to and from the transducer, a signal processor operable to send and receive electrical signals to and from said transducer, the drive cable being electrically connected to the signal processor for conducting pulses to and from the signal processor, and the drive cable further comprising:

a rotatable outer layered coil assembly;
   a core wire located inside of said layered coil assembly and connected thereto for rotation therewith; and
   wherein said outer layered coil assembly further comprises a plurality of coaxial coil layers around said core wire
   wherein said outer layered coil assembly further is comprised of at least one layer of flat wire.

3. The drive cable of claim 1 in which each of said coil layers is comprised of a plurality of individual strands of flat wire helically wound.

4. A drive cable for use in an imaging device for ultrasonic imaging of small vessels of a patient's body, the imaging device having an elongate member with a distal end positionable within a small vessel of the patient's body and a proximal end positionable outside the body, a transducer located at a distal end of the elongate member and operable to scan the vessel walls, the drive cable being electrically connected to a proximal end of the transducer for conducting pulses to and from the transducer, a signal processor operable to send and receive electrical signals to and from said transducer, the drive cable being electrically connected to the signal processor for conducting pulses to and from the signal processor, and the drive cable further comprising:

a rotatable outer layered coil assembly;
   a core wire located inside of said layered coil assembly and connected thereto for rotation therewith; and
   wherein said outer layered coil assembly further comprises a plurality of coaxial coil layers around said core wire;
   wherein each layer of said plurality of coil layers is comprised of multiple individual strands of wires.

5. A drive cable for use in an imaging device for ultrasonic imaging of small vessels of a patient's body, the imaging device having an elongate member with a distal end positionable within a small vessel of the patient's body and a proximal end positionable outside the body, a transducer located at a distal end of the elongate member and operable to scan the vessel walls, the drive cable being electrically connected to a proximal end of the transducer for conducting pulses to and from the transducer, a signal processor operable to send and receive electrical signals to and from said transducer, the drive cable being electrically connected to the signal processor for conducting pulses to and from the signal processor, and the drive cable further comprising:

a rotatable outer layered coil assembly;
   a core wire located inside of said layered coil assembly and connected thereto for rotation therewith; and
   wherein said outer layered coil assembly further comprises a plurality of coaxial coil layers around said core wire;
   wherein each layer of said plurality of individual layers is wound in an opposite helical direction from the layer immediately adjacent thereto.

6. An intravascular drive cable imaging device for ultrasonic imaging of small vessels of a patient's body and a proximal end positionable outside the body, a transducer located at a distal end of the imaging device and operable to scan the vessel walls, the drive cable being electrically connected to a proximal end of the transducer for conducting pulses to and from the transducer, a signal processor operable to send and receive electrical signals to and from said transducer, the drive cable being operatively adapted for conducting pulses to and from the signal processor, and the drive cable further comprising:

a rotatable outer layered coil assembly; and coil assembly and connected thereto for rotation therewith;

wherein said core wire comprises a coaxial cable having an internal conductor and a external conductor separated from said internal conductor by an insulator.

7. The drive cable of claim 6 in which said external conductor comprises:

a braided shield formed of a plurality of wires.

8. The drive cable of claim 7 in which said braided shield is comprised of a plurality of flat wires.

9. The drive cable of claim 6 in which said external conductor includes a plating of a high conductivity material.

10. In an imaging device for ultrasonic imaging of small vessels of a patient's body, the imaging device having an elongate member with a distal end positionable within an intravascular vessel while a proximal end is located outside the body, a transducer located at a distal end of the elongate member and operable to scan the vessel with ultrasonic pulses, a distal drive cable connected at a distal end thereof to the transducer and operable to transmit electrical signals to and from said transducer, a proximal drive cable, a signal processor connected to a proximal end Of the proximal drive cable for generating and receiving pulses to and from the transducer, a motor connected to the proximal end of the proximal drive cable to rotate the transducer, and a coupling member for connecting the distal drive cable and the proximal drive cable, the coupling member further comprising:

a distal section connected to the elongate member and to the proximal end of the distal drive cable and adapted to allow rotational movement between the elongate member and the distal drive cable, and a proximal section releasably connectable to the distal section, said proximal section connected the proximal drive cable;

a sleeve portion connected to the elongate member, and a first rotating coaxial member located inside said sleeve portion connected to the distal drive cable.

11. The coupling member of claim 10 in which the proximal portion comprises:

a sleeve portion connected to the proximal drive cable;

a second rotating coaxial member located inside said sleeve portion, said second rotating member matably engageable with said first rotating coaxial member;

an electrical signal transfer apparatus connected to said second rotating coaxial member for transferring the electrical signal from the second rotatable coaxial member to a stationary electrical conductor; and a rotating drive shaft connected proximally to the motor and distally to the second rotatable coaxial member.

12. The coupling member of claim 11 in which the electric signal transfer apparatus comprises:

a first conductor connected to said second rotating coaxial member; and a second conductor slidably engaged against the first conductor whereby an electrical signal can be transmitted to and from said first to said second conductors.

13. The coupling member of claim 12 in which said conductors are a brush and slip ring.

14. A data processing architecture for use in an imaging device for ultrasonic imaging of a small vessel of a patient's body, the imaging device having an elongate member with a distal end positionable within the small vessel and a proximal end positionable outside the body, a transducer located at a distal end of the elongate member and operable to scan the vessel walls, a drive cable connected to the transducer and operable to transmit electrical signal to and from the transducer, and a signal processor connected to a proximal end of the drive cable for generating and receiving pulses to and from the transducer, the data processing architecture comprising:

a raw data pipeline adapted to process polar coordinate data derived from the signals produced by the transducer:

a means responsive to the raw data pipeline and a look up table for converting data from the raw data pipeline to rectangular coordinate data and outputting rectangular coordinate data; and a graphics data pipeline responsive to the output of the converting means.

15. A data processing architecture as defined in claim 14 further comprising a high speed data acquisition circuit operatively connected to the raw data pipeline for synchonizing the raw data pipeline and transferring data down said raw data pipeline at a slower speed than a speed at which data is transferred on said raw data pipeline.

16. A data processing architecture as defined in claim 14 wherein at least one of raw data enhancement and feature extraction is performed in the raw data pipeline.

17. A data processing architecture as defined in claim 14 wherein at least one of deconvolution, Fourier transform processing, neurocomputing processing is performed in the raw data pipeline.

18. A data processing architecture as defined in claim 14 wherein at least one of edge detection, area calculation, area manipulation, logical pixel edge smoothing, and image overlay is performed in the graphics data pipeline.

19. A data processing architecture as defined in claim 14 further comprising a parallel data pipeline branched off of at least one of the raw data pipeline and the graphics data pipeline.

* * * * *

UNITED STATES PATENT AND TRADEMARK OFFICE
CERTIFICATE OF CORRECTION

PATENT NO. : 5,438,997
DATED : August 8, 1995
INVENTOR(S) : Wayne Sieben and Mark J. Whalen It is certified that error appears in the above-identified patent and that said Letters Patent is hereby corrected as shown below:

On the cover page, [57] ABSTRACT, line 2, before the word "manufacture", please delete "an", and insert therefor --and--

In column 2, line 25, please delete the words "cross sectional", and insert therefor --cross-sectional--

In column 4, line 10, after the word "use", please delete the word "an", and insert therefor --and--

In column 4, line 40, after "7a", please insert the word --is--

In column 4, line 44, after "7b", please insert the word --is--

In column 4, lines 40 and 44, please delete the word "alone", and insert therefor --along--

In column 5, lines 21, 23, and 25, after the word "is", please insert --a--

In column 5, line 30, please delete the words "cross sectional", and insert therefor --cross-sectional--

UNITED STATES PATENT AND TRADEMARK OFFICE
CERTIFICATE OF CORRECTION

PATENT NO. : 5,438,997

DATED : August 8, 1995

INVENTOR(S) : Wayne Sieben and Mark J. Whalen

It is certified that error appears in the above-identified patent and that said Letters Patent is hereby corrected as shown below:

In column 5, line 32, after the words "view of", please delete "a"

In column 6, line 21, before the word "present", please insert the word --the--

In column 7, line 13, please delete "Mhz", and insert therefor --MHz--

In column 9, line 23, please delete the words "cross-section", and insert therefor --cross section--

In column 11, line 40, please delete the words "cross-section", and insert therefor --cross section--

In column 15, line 61, please delete "Mhz", and insert therefor --MHz--

UNITED STATES PATENT AND TRADEMARK OFFICE
CERTIFICATE OF CORRECTION

PATENT NO. : 5,438,997

DATED : August 8, 1995

INVENTOR(S) : Wayne Sieben and Mark J. Whalen

It is certified that error appears in the above-identified patent and that said Letters Patent is hereby corrected as shown below:

In column 16, line 44, please delete "has 80", and insert therefor --80 has--

In column 17, line 62, please delete the word "degree", and insert therefor --degrees--

In column 18, line 66, before the word "interfere", please insert the word --to--

In column 19, line 49, please delete the word "complimentary", and insert therefor --complementary--

In column 21, line 27, please delete the word "pain", and insert therefor --pair--

In column 26, line 60, please delete "Db", and insert therefor --dB--

In column 31, line 37, before the words "this technique", please insert the word --with--

In column 32, line 47, please delete the word "indexing", and insert therefor --Indexing--

UNITED STATES PATENT AND TRADEMARK OFFICE
CERTIFICATE OF CORRECTION

PATENT NO. : 5,438,997

DATED : August 8, 1995

INVENTOR(S) : Wayne Sieben and Mark J. Whalen

It is certified that error appears in the above-identified patent and that said Letters Patent is hereby corrected as shown below:

In column 32, line 55, please delete "insider", and insert therefor --inside--

In column 32, line 59, please delete the word "posess", and insert therefor --possess--

In column 32, line 59, after the word "could", please delete the word "be"

In column 32, line 62, please delete the word "Just", and insert therefor --just--

In column 34, line 14, please delete the word "buss", and insert therefor --bus--

In column 34, line 35, please delete the word "fourier", and insert therefor --Fourier--

In column 34, line 56, after the word "structure", please delete the word "is"

In column 35, line 57, please delete the word "though", and insert therefor --through--

UNITED STATES PATENT AND TRADEMARK OFFICE
CERTIFICATE OF CORRECTION

PATENT NO.   :   5,438,997

DATED        :   August 8, 1995

INVENTOR(S)  :   Wayne Sieben and Mark J. Whalen

It is certified that error appears in the above-identified patent and that said Letters Patent is hereby corrected as shown below:

In column 36, line 35, after the word "far", please insert the word --as--

In column 36, line 43, please delete the word "fourier", and insert therefor --Fourier--

In column 39, line 10, before the word "connected", please delete the word "and"

In column 39, line 34, after the word "end", please delete the word "Of", and insert therefor --of--

In column 39, line 46, after the word "connected", please insert the word --to--

Signed and Sealed this

Seventh Day of May, 1996

Attest:

BRUCE LEHMAN

*Attesting Officer*         Commissioner of Patents and Trademarks